(12) United States Patent
Kim et al.

(10) Patent No.: US 12,090,248 B2
(45) Date of Patent: Sep. 17, 2024

(54) CROSSLINKED HYALURONIC ACID, HYALURONIC ACID HYDROGEL, AND METHOD FOR PRODUCING CROSSLINKED HYALURONIC ACID AND HYALURONIC ACID HYDROGEL

(71) Applicant: HANMI PHARM. CO., LTD, Hwaseong-si (KR)

(72) Inventors: Soo Jin Kim, Hwaseong-si (KR); Se Kweon Kim, Pyeongtaek-si (KR); Chung Leol Shin, Pyeongtaek-si (KR); Hyo Seung Park, Icheon (KR); Yong Woo Kim, Pyeongtaek-si (KR); Back Ho Lee, Pyeongtaek-si (KR); Jun Young Kim, Pyeongtaek-si (KR)

(73) Assignee: HANMI PHARM. CO., LTD., Hwaseong-si (KR)

( * ) Notice: Subject to any disclaimer, the term of this patent is extended or adjusted under 35 U.S.C. 154(b) by 338 days.

(21) Appl. No.: 17/311,070

(22) PCT Filed: Dec. 6, 2019

(86) PCT No.: PCT/KR2019/017210
§ 371 (c)(1),
(2) Date: Jun. 4, 2021

(87) PCT Pub. No.: WO2020/116999
PCT Pub. Date: Jun. 11, 2020

(65) Prior Publication Data
US 2022/0040374 A1    Feb. 10, 2022

(30) Foreign Application Priority Data

Dec. 7, 2018 (KR) .................. 10-2018-0156801
Dec. 6, 2019 (KR) .................. 10-2019-0161388

(51) Int. Cl.
| | |
|---|---|
| *A61L 27/20* | (2006.01) |
| *A61L 27/52* | (2006.01) |
| *C08B 37/08* | (2006.01) |
| *C08J 3/14* | (2006.01) |
| *C08J 3/24* | (2006.01) |
| *C08L 5/08* | (2006.01) |

(52) U.S. Cl.
CPC .............. *A61L 27/20* (2013.01); *A61L 27/52* (2013.01); *C08B 37/0072* (2013.01); *C08J 3/14* (2013.01); *C08J 3/24* (2013.01); *C08L 5/08* (2013.01); *C08J 2305/08* (2013.01); *C08L 2203/02* (2013.01)

(58) Field of Classification Search
None
See application file for complete search history.

(56) References Cited

U.S. PATENT DOCUMENTS

| | | | |
|---|---|---|---|
| 4,713,448 A | 12/1987 | Balazs et al. | |
| 7,456,220 B2 * | 11/2008 | Calias .................... | A61K 31/17 514/588 |
| 9,216,193 B2 | 12/2015 | Hashimoto et al. | |
| 10,077,320 B2 | 9/2018 | Karlsson et al. | |
| 2019/0315887 A1 | 10/2019 | Choi et al. | |

FOREIGN PATENT DOCUMENTS

| | | | | |
|---|---|---|---|---|
| CN | 104623730 A | 5/2015 | | |
| CN | 105473623 A | 4/2016 | | |
| CN | 105670011 A | 6/2016 | | |
| JP | 2016-523303 A | 8/2016 | | |
| KR | 10-2007-0004159 A | 1/2007 | | |
| KR | 10-2008-0073419 A | 8/2008 | | |
| KR | 10-2014-0000206 A | 1/2014 | | |
| KR | 10-2015-0008556 A | 1/2015 | | |
| KR | 10-2017-0090965 A | 8/2017 | | |
| WO | WO-2014206701 A1 * | 12/2014 | ........... | A61K 31/728 |
| WO | 2017/131298 A1 | 8/2017 | | |

OTHER PUBLICATIONS

Japanese Office Action issued Aug. 7, 2023 in JP Application No. 2021-532294.
International Searching Authority, International Search Report for PCT/KR2019/017210 dated, Mar. 31, 2020 (PCT/ISA/210).
Communication dated Aug. 23, 2023 issued by the State Intellectual Property Office of the P.R.China in application No. 201980081130.3.
Lei, S., et al. "Research on Extraction and Purification of Hyaluronic Acid from Fermentation Broth" Shangdong Agricultural Sciences, 2017, vol. 49, No. 3, pp. 134-139.
Tan, Z., et al., "Animal Drugs extraction and manufacturing for practical Technology", 1st edition, p. 251, China Agricultural Publishing Company, Dec. 31, 2000 (6 pages).

* cited by examiner

*Primary Examiner* — Dale R Miller
(74) *Attorney, Agent, or Firm* — Sughrue Mion, PLLC

(57) ABSTRACT

Provided are a crosslinked hyaluronic acid product in the form of powder and a method of preparing the same, and a crosslinked hyaluronic acid hydrogel prepared using the crosslinked hyaluronic acid product in the form of powder, and a method of preparing the same. The crosslinked hyaluronic acid hydrogel according to the present disclosure exhibits excellent rheological properties, and mass production thereof is easy and quality uniformity thereof is excellent.

14 Claims, 11 Drawing Sheets

CROSSLINKED HYALURONIC ACID, HYALURONIC ACID HYDROGEL, AND METHOD FOR PRODUCING CROSSLINKED HYALURONIC ACID AND HYALURONIC ACID HYDROGEL

CROSS REFERENCE TO RELATED APPLICATIONS

This application is a National Stage of International Application No. PCT/KR2019/017210 filed Dec. 6, 2019, claiming priority based on Korean Patent Application No. 10-2018-0156801 filed on Dec. 7, 2018 and Korean Patent Application No. 10-2019-0161388 filed on Dec. 6, 2019.

TECHNICAL FIELD

The present disclosure relates to a crosslinked hyaluronic acid product, a hyaluronic acid hydrogel, and a method of preparing the same.

BACKGROUND ART

Hyaluronic acid is a biopolymeric material in which repeating units consisting of N-acetyl-D-glucosamine and D-glucuronic acid are linearly connected. Hyaluronic acid is known to be abundant in the placenta of animals, the vitreous humor of the eyeball, synovial fluid of joints, cockscombs, etc. Further, hyaluronic acid is known to be produced by fermentation by microorganisms of the genus *Streptococcus* (e.g., *Streptococcus equi*, or *Streptococcus zooepidemecus*) or microorganisms of the genus *Staphylococcus*.

SYNVISC-ONE®, which is an injectable crosslinked hyaluronic acid product that lasts for 6 months with only Single-injection treatment, is currently commercially available in the United States. Synvisc-one® includes a crosslinked hyaluronic acid product, which is obtained by extracting hyaluronic acid from cockscombs with a formalin-containing aqueous solution, and has low viscoelasticity, because proteins linked to hyaluronic acid are weakly crosslinked by formalin (Patent Document 1). The weakly crosslinked hyaluronic acid is additionally crosslinked by a crosslinking agent, divinyl sulfone (DVS), and is combined with the crosslinked hyaluronic acid product having increased viscoelasticity, to form a complex hyaluronic acid crosslinked product (SYNVISC-ONE®) with viscoelasticity suitable for application to a joint cavity of the human body.

However, it is difficult to filter existing crosslinked hyaluronic acid products, and thus a lot of effort is required to remove foreign substances contained in the gel, and a large amount of washing buffer is required to wash the crosslinking agent. In addition, the existing crosslinked hyaluronic acid products have a lot of problems in quality uniformity due to severe variations in rheological properties of hyaluronic acid, such as viscoelasticity, etc., according to each production batch. Therefore, quality control is not easy, and a complex process and a lot of cost are required for mass production.

PRIOR ART DOCUMENTS

Patent Documents (Patent Document 1) U.S. Pat. No. 4,713,448
(Patent Document 2) Korean Patent Publication No. 10-2017-0090965

DESCRIPTION OF EMBODIMENTS

Technical Problem

An aspect of the present disclosure relates to a method of preparing a crosslinked hyaluronic acid product in the form of powder, which is economical and optimized for mass production.

Another aspect of the present disclosure relates to a crosslinked hyaluronic acid product in the form of powder, which is economical and optimized for mass production.

Still another aspect of the present disclosure relates to a method of preparing a crosslinked hyaluronic acid hydrogel which exhibits excellent rheological properties and quality uniformity.

Still another aspect of the present disclosure relates to a crosslinked hyaluronic acid hydrogel which exhibits excellent rheological properties and quality uniformity.

Solution to Problem

The present disclosure provides a method of preparing a crosslinked hyaluronic acid product in the form of powder, which is economical and optimized for mass production.

The method of preparing a crosslinked hyaluronic acid product in the form of powder of the present disclosure may include
  preparing an aqueous solution including hyaluronic acid, a salt thereof, or a mixture thereof;
  adding a crosslinking agent to the aqueous solution to cause a crosslinking reaction of the hyaluronic acid to occur; and
  adding ethanol to the aqueous solution to solidify the hyaluronic acid into particles.

In one specific embodiment, the crosslinking reaction may be performed by adding a crosslinking agent to the aqueous solution including hyaluronic acid, a salt thereof, or a mixture thereof and causing a crosslinking reaction to occur at 10° C. to 40° C., for example, at 25° C. to 35° C., for 2 hours to 8 hours, for example, for 4 hours to 6 hours under stirring at 50 rpm to 350 rpm, for example, at 150 rpm to 350 rpm, for example, at 250 rpm.

With regard to the method of the present disclosure, when ethanol is added to the aqueous solution, an ethanol addition rate may be 20 mL/min to 1000 mL/min.

With regard to the method of the present disclosure, when ethanol is added to the aqueous solution, a rate of volume change of ethanol with respect to the total volume of the mixed solution may be 0.5% (v/v)/min to 35% (v/v)/min.

In exemplary embodiments of the present disclosure, the aqueous solution may include the crosslinking agent in an amount of 10 µl to 500 µl with respect to 1 g of hyaluronic acid, a salt thereof, or a mixture thereof.

In exemplary embodiments of the present disclosure, a volume ratio of the aqueous solution and ethanol added to the aqueous solution may be 1:1 to 10.

In exemplary embodiments of the present disclosure, the method may further include causing a crosslinking reaction of the aqueous solution including hyaluronic acid particles to occur. The crosslinking reaction may be maintained by the crosslinking agent which is added to the aqueous solution. In the crosslinking reaction, the aqueous solution including hyaluronic acid particles may be further crosslinked with the crosslinking agent which remains in the aqueous solution after reaction.

In one specific embodiment, the additional crosslinking reaction may be performed by causing the crosslinking reaction of the aqueous solution including hyaluronic acid particles to occur at 15° C. to 30° C., for example, at 25° C., for 24 hours or less under stirring at 50 rpm to 350 rpm, for example, at 250 rpm. During the additional crosslinking reaction, the stirring speed may be the same as that during the crosslinking reaction before ethanol addition.

In exemplary embodiments of the present disclosure, the method may further include washing the crosslinked hyaluronic acid product obtained by solidifying into hyaluronic acid particles after the crosslinking reaction, or the crosslinked hyaluronic acid product obtained by additionally crosslinking with the crosslinking agent remaining in the aqueous solution with ethanol or a solution containing ethanol.

In exemplary embodiments of the present disclosure, the crosslinked hyaluronic acid product in the form of powder may exhibit a particle size distribution D90 of 80 µm or less.

In exemplary embodiments of the present disclosure, the crosslinked hyaluronic acid product in the form of powder may exhibit particle size distributions D10 of 2.5 µm to 6 µm, D50 of 8 µm to 20 µm, and D90 of 25 µm to 80 µm.

The present disclosure provides a crosslinked hyaluronic acid product in the form of powder, which is prepared by the above methods.

In exemplary embodiments of the present disclosure, the crosslinked hyaluronic acid product may exhibit viscoelasticity similar to, stability equivalent to or higher than, and degree of modification (MoD) equivalent to or higher than those of a commercially available product, such as Synvisc-one®. In exemplary embodiments of the present disclosure, the crosslinked hyaluronic acid product may exhibit increased pendant MoD (%), crosslink MoD (%), and total MoD (%), as compared with natural hyaluronic acid(HA) or SYNVISC-ONE®.

In exemplary embodiments of the present disclosure, MoD of the hyaluronic acid (HA) may be analyzed using an HPLC system. In the analysis method, HA (repeating units consisting of glucuronic acid and N-acetyl-D-glucosamine) which is a polysaccharide is digested with hyaluronidase to form a smaller polymer, and modified HA by the crosslinking agent and unmodified HA may be distinguished from each other by a difference in chromatograms and by comparing their MoDs with each other. In the analysis method, HA is digested with hyaluronidase (Hyaluronidase obtained from *Streptomyces* hyalurolyticus) under conditions of pH 5.0 and 36° C., and then saccharide units thus digested may be measured at UV absorbance (232 nm) using a DIONEX CARBOPAC PA100 (Thermo Scientific) HPLC column. When hyaluronic acid is fully digested with hyaluronidase, it produces a tetramer and a hexamer, and crosslinked hyaluronic acid produces saccharide units slightly larger than the tetramer and the hexamer, or oligomers larger than those, etc., which may be shown in chromatograms. MoD may be obtained by the area of each chromatogram, and peaks of higher-order oligomers larger than octamers may be distinguished by crosslink MoD (%), and peaks of oligomers smaller than octamers, excluding main peaks of tetramer and hexamer, may be distinguished by pendant MoD (%), and both of them are combined as total MoD (%).

The crosslinked hyaluronic acid product may exhibit an increase in MoD (%), as more crosslinking reaction occurs. In addition, the hyaluronic acid produced by the excessive crosslinking reaction may have a structure that is not capable of absorbing sufficient water. In exemplary embodiments of the present disclosure, the crosslinked hyaluronic acid product may exhibit 0.1% to 10% of total MoD (%). In addition, the crosslinked hyaluronic acid product that satisfies the above MoD may have a structure capable of absorbing sufficient water and may exhibit a viscoelasticity value capable of exhibiting sufficient hydration.

The present disclosure provides a method of preparing a crosslinked hyaluronic acid hydrogel which exhibits excellent rheological properties and quality uniformity.

The method of preparing the crosslinked hyaluronic acid hydrogel of the present disclosure may include
  preparing an aqueous solution including hyaluronic acid, a salt thereof, or a mixture thereof;
  adding a crosslinking agent to the aqueous solution to cause a crosslinking reaction of the hyaluronic acid to occur;
  adding ethanol to the aqueous solution to solidify the hyaluronic acid into particles;
  maintaining the crosslinking reaction of the aqueous solution including the hyaluronic acid particles to prepare a crosslinked hyaluronic acid product in the form of powder; and
  hydrating the prepared crosslinked hyaluronic acid product in the form of powder.

With regard to the method of the present disclosure, when ethanol is added to the aqueous solution, an ethanol addition rate may be 20 mL/min to 1000 mL/min.

With regard to the method of the present disclosure, when ethanol is added to the aqueous solution, the rate of volume change of ethanol with respect to the total volume of the mixed solution may be 0.5% (v/v)/min to 35% (v/v)/min.

In exemplary embodiments of the present disclosure, the hydration may be performed by adding the crosslinked hyaluronic acid product in the form of powder to water or a solution comprising water.

In exemplary embodiments of the present disclosure, the crosslinked hyaluronic acid product in the form of powder may be added in an amount of 5 mg to 15 mg with respect to 1 mL of water or the solution comprising water.

In exemplary embodiments of the present disclosure, the crosslinked hyaluronic acid hydrogel may exhibit a particle size distribution D90 of 240 µm or less.

In exemplary embodiments of the present disclosure, the crosslinked hyaluronic acid hydrogel may exhibit particle size distributions D10 of 25 µm to 40 µm, D50 of 70 µm to 110 µm, and D90 of 190 µm to 240 µm.

In exemplary embodiments of the present disclosure, the method may further include filtering the crosslinked hyaluronic acid hydrogel using a filter.

In exemplary embodiments of the present disclosure, the crosslinked hyaluronic acid hydrogel after the filtration may exhibit a particle size distribution D90 of 120 µm or less.

In exemplary embodiments of the present disclosure, the crosslinked hyaluronic acid hydrogel after filtration may exhibit particle size distributions D10 of 10 µm to 30 µm, D50 of 35 µm to 65 µm, and D90 of 80 µm to 120 µm.

The present disclosure provides a crosslinked hyaluronic acid hydrogel prepared by the above methods.

In exemplary embodiments of the present disclosure, the crosslinked hyaluronic acid hydrogel may have elasticity of 30 Pa to 200 Pa and viscosity of 10 Pa to 100 Pa.

The present disclosure provides an amorphous crosslinked hyaluronic acid hydrogel. The hyaluronic acid hydrogel may have an X-ray powder diffraction pattern (XRD) as shown in FIG. 5.

In exemplary embodiments of the present disclosure, the hyaluronic acid hydrogel may exhibit a particle size distribution D90 of 120 µm or less.

In exemplary embodiments of the present disclosure, the hyaluronic acid hydrogel may exhibit particle size distributions D10 of 10 μm to 30 μm, D50 of 35 μm to 65 μm, and D90 of 80 μm to 120 μm.

In exemplary embodiments of the present disclosure, the crosslinked hyaluronic acid hydrogel may have elasticity of 30 Pa to 200 Pa and viscosity of 10 Pa to 100 Pa.

In exemplary embodiments of the present disclosure, the crosslinked hyaluronic acid hydrogel may have elasticity of 100 Pa to 150 Pa and viscosity of 10 Pa to 60 Pa.

In exemplary embodiments of the present disclosure, the crosslinked hyaluronic acid hydrogel may have a modulus of elasticity reduction of 30% or less, when stored at 25° C. for 8 months. In exemplary embodiments of the present disclosure, the crosslinked hyaluronic acid hydrogel may have a modulus of elasticity reduction of 25% or less, when stored at 30° C. for 8 months. In exemplary embodiments of the present disclosure, the crosslinked hyaluronic acid hydrogel may have a modulus of elasticity reduction of 40% or less, when stored at 40° C. for 8 months. In exemplary embodiments of the present disclosure, the crosslinked hyaluronic acid hydrogel may have a modulus of elasticity reduction of 90% or less, when stored at 60° C. for 8 months.

In exemplary embodiments of the present disclosure, the crosslinked hyaluronic acid hydrogel may have a modulus of viscosity reduction of 35% or less, when stored at 25° C. for 8 months. In exemplary embodiments of the present disclosure, the crosslinked hyaluronic acid hydrogel may have a modulus of viscosity reduction of 20% or less, when stored at 30° C. for 8 months. In exemplary embodiments of the present disclosure, the crosslinked hyaluronic acid hydrogel may have a modulus of viscosity reduction of 18% or less, when stored at 40° C. for 8 months. In exemplary embodiments of the present disclosure, the crosslinked hyaluronic acid hydrogel may have a modulus of viscosity reduction of 50% or less, when stored at 60° C. for 8 months.

Hyaluronic acid may have reduced viscoelasticity and rheological properties due to degradation and reduction of polymer chains by factors such as temperature, enzymes, etc., and as a result, viscosupplementation performance thereof may be deteriorated. In contrast, the crosslinked hyaluronic acid has improved degradation resistance, and thus its maintenance period in the body may be improved, as compared with non-crosslinked hyaluronic acid. In exemplary embodiments of the present disclosure, the crosslinked hyaluronic acid hydrogel may have improved degradation resistance, as compared with hyaluronic acid, and may have improved degradation resistance, as compared with non-crosslinked hyaluronic acid.

Advantageous Effects of Disclosure

A crosslinked hyaluronic acid product in the form of powder of the present disclosure has a uniform degree of crosslinking, may be easily washed with a small amount of a washing solution, and has excellent quality uniformity. Further, a crosslinked hyaluronic acid hydrogel prepared using the crosslinked hyaluronic acid product in the form of powder may be filtered using a filter having a small pore size, and thus foreign substances may be easily removed, and the quality uniformity is excellent. Therefore, the crosslinked hyaluronic acid product in the form of powder according to the present disclosure and the crosslinked hyaluronic acid hydrogel prepared using the same are suitable for mass production and are economical.

MODE OF DISCLOSURE

Figure 1:
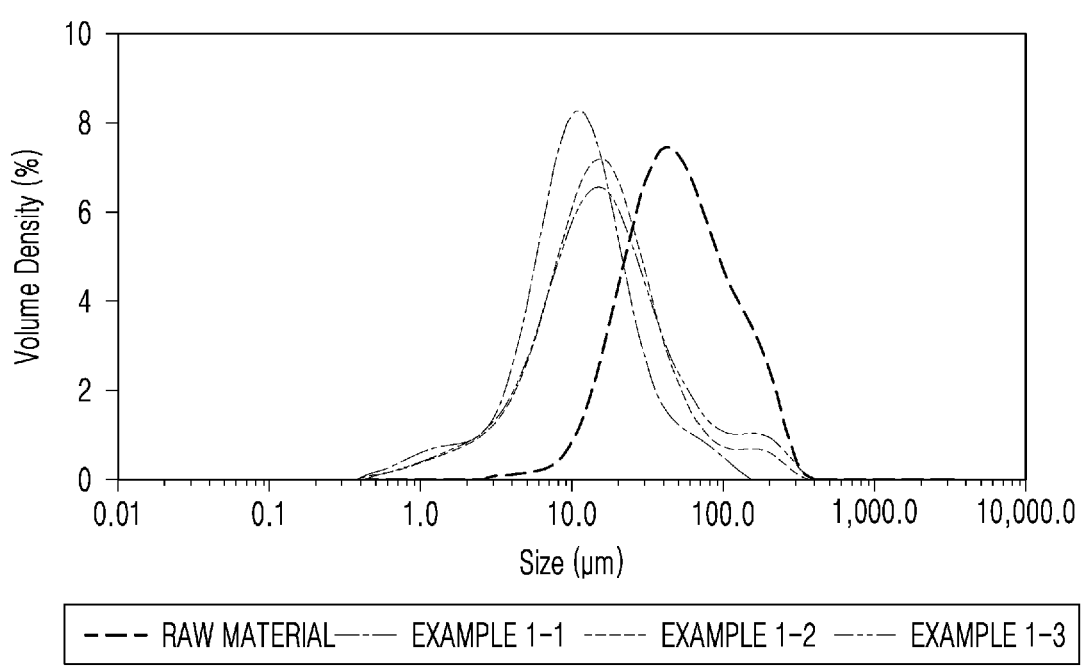
FIG. 1 shows particle size distributions of sodium hyaluronate as a raw material and crosslinked hyaluronic acid products in the form of powder according to Examples 1-1 to 1-3, wherein the vertical axis represents volume density (%), and the horizontal axis represents particle size (μm)

Hereinafter, the present disclosure will be described in more detail.

Unless defined otherwise, all technical terms used herein have the same meanings as those generally understood by one of ordinary skill in the art to which the present disclosure belongs. Further, although methods or samples are described herein, those similar or equivalent thereto are also incorporated in the scope of the present disclosure. The contents of all the publications disclosed as references herein are incorporated in the present disclosure.

In the present disclosure, DX is Y, which means that when the particle size of hyaluronic acid, a hyaluronic acid gel, or a crosslinked hyaluronic acid hydrogel in the form of powder is represented by a cumulative curve, the particle size, at the point where cumulative undersized particles becomes X % (% is calculated, based on the number, volume, or weight), is Y. For example, D10 represents the particle size of particles, at the point where cumulative undersized particles of hyaluronic acid, a hyaluronic acid gel, or a crosslinked hyaluronic acid hydrogel in the form of powder becomes 10%, D50 represents the particle size of particles, at the point where cumulative undersized particles of hyaluronic acid, a hyaluronic acid gel, or a crosslinked hyaluronic acid hydrogel in the form of powder becomes 50%, and D90 represents the particle size of particles, at the point where cumulative undersized particles of hyaluronic acid, a hyaluronic acid gel, or a crosslinked hyaluronic acid hydrogel in the form of powder becomes 90%.

Whether the particle size distribution DX represents the percentage of the total cumulative particles, based on which of the number, volume, or weight, depends on a method used to measure the particle size distribution. The method of measuring the particle size distribution and the type of % associated therewith are known to those skilled in the art. For example, when the particle size distribution is measured by a well-known laser diffraction method, the X value in DX may represent the percentage calculated by the volume average. It is well known to those skilled in the art that results of measuring the particle size distribution obtained by a specific method may be correlated with those obtained from other techniques based on experience by routine experiments. For example, the laser diffraction method is sensitive to the volume of particles to provide a volume average particle size, which corresponds to a weight average particle size, if the density is constant.

In the present disclosure, viscoelasticity refers to a storage modulus (G') and a loss modulus (G"). The viscoelasticity is measured using a rotational rheometer. When dynamic viscoelasticity is measured, a geometry with a diameter of 20 mm is used, a measurement distance (GAP) between the geometry and a plate is 0.5 mm, the temperature is maintained at 25° C. until the end of the analysis, frequency oscillation is used as a control program, and frequency is set in the range from 0.1 Hz to 10 Hz to measure the storage modulus and loss modulus. In the present disclosure, storage modulus (G') may be represented by elasticity, and loss modulus (G") may be represented by viscosity.

The method of preparing a crosslinked hyaluronic acid product in the form of powder of the present disclosure may include preparing an aqueous solution including hyaluronic acid, a salt thereof, or a mixture thereof;

adding a crosslinking agent to the aqueous solution to cause a crosslinking reaction of the hyaluronic acid to occur; and adding ethanol to the aqueous solution to solidify the hyaluronic acid into particles.

With regard to the method, when ethanol is added to the aqueous solution, the ethanol is slowly added over a predetermined time.

According to the preparation method of the present disclosure, when ethanol is slowly added to the aqueous solution over a predetermined time, solid hyaluronic acid is produced in the form of fine particles having a uniform particle size, and the solid-state hyaluronic acid particles are reacted with the crosslinking agent and a uniform crosslinking reaction occurs. Therefore, a crosslinked hyaluronic acid product in the form of powder with a uniform degree of crosslinking may be produced, and a crosslinked hyaluronic acid product may be obtained in each preparation process, the crosslinked hyaluronic acid product having a fine particle size at the level of powder while having appropriate and uniform physical properties, such as particle size, viscosity, elasticity, etc. As a result, it is possible to repeatedly mass-produce, with reproducibly, a crosslinked hyaluronic acid product having the particle size, viscosity, and elasticity showing optimal effects.

A rate at which ethanol is added to the aqueous solution may be controlled such that solid hyaluronic acid produced by the addition of ethanol may be produced in the form of particles. Specifically, it is possible to produce a crosslinked hyaluronic acid product having a target particle size of solid hyaluronic acid and physical properties by controlling the rate of change of the ethanol concentration in the total reaction solution according to the ethanol addition rate.

In exemplary embodiments of the present disclosure, the aqueous solution including hyaluronic acid, a salt thereof, or a mixture thereof may be prepared by adding the hyaluronic acid, the salt thereof, or the mixture thereof to an alkaline aqueous solution including basic materials.

In the present disclosure, the hyaluronic acid may refer to hyaluronic acid itself, a salt of hyaluronic acid, or a mixture thereof. Therefore, the aqueous solution including hyaluronic acid may refer to an aqueous solution including hyaluronic acid, a salt thereof, or a mixture thereof. In addition, hyaluronic acid particles may refer to particles produced using hyaluronic acid, a salt thereof, or a mixture thereof.

The salt of hyaluronic acid may be in any salt form suitable for application to a living body, and specifically, it may be an alkali salt, an alkaline earth metal salt, an amino acid salt, a salt with an organic base, or a mixture thereof. For example, the salt of hyaluronic acid may be selected from the group consisting of sodium hyaluronate, calcium hyaluronate, potassium hyaluronate, magnesium hyaluronate, zinc hyaluronate, cobalt hyaluronate, a tetrabutylammonium salt of hyaluronic acid, diethanolamine hyaluronate, cyclohexylamine hyaluronate, and any combination thereof. In one specific embodiment, the salt of hyaluronic acid may be sodium hyaluronate.

The hyaluronic acid or the salt thereof may have a molecular weight of about 100,000 Da to about 6,000,000 Da, and in one specific embodiment, the hyaluronic acid or sodium hyaluronate may have a molecular weight of about 100,000 Da to about 6,000,000 Da, specifically about 500,000 Da to about 6,000,000 Da, and more specifically, about 1,000,000 Da to about 4,000,000 Da.

The hyaluronic acid may include any hyaluronic acid known in the art, and hyaluronic acid obtained from any raw material may be used. The hyaluronic acid may be hyaluronic acid derived from animals (e.g., placenta of animals or cockscombs), or any microorganism capable of producing hyaluronic acid during fermentation (e.g., a microorganism of the genus *Staphylococcus* or a microorganism of the genus *Streptococcus*).

In one specific embodiment, the hyaluronic acid may be hyaluronic acid derived from a microorganism, for example, hyaluronic acid derived from a microorganism of the genus *Streptococcus*. Hyaluronic acid derived from microorganisms has advantages in terms of quality control during preparation into pharmaceutical products because it may be free from virus problems of hyaluronic acid derived from animals or uniformity problem of raw material quality.

The aqueous solution including hyaluronic acid, a salt thereof, or a mixture thereof may be an aqueous alkaline solution including any basic material which is known to be applicable in the preparation of crosslinked hyaluronic acid products. For example, the aqueous alkaline solution may be an aqueous alkaline solution at pH of 9 to 13, and the aqueous alkaline solution may be a sodium hydroxide-containing aqueous solution, a potassium hydroxide-containing aqueous solution, or an ammonia-containing aqueous solution, and in one specific embodiment, the aqueous alkaline solution may be a sodium hydroxide-containing aqueous solution.

In exemplary embodiments of the present disclosure, the aqueous solution including hyaluronic acid, a salt thereof, or a mixture thereof may include hyaluronic acid, the salt thereof, or the mixture thereof in a volume of about 0.5% (w/v) to about 5% (w/v), and specifically, about 1% (w/v) to about 4% (w/v), based on the total volume of the aqueous solution. In one specific embodiment, the aqueous solution including hyaluronic acid, a salt thereof, or a mixture thereof may include sodium hyaluronate in a volume of about 2% (w/v).

In exemplary embodiments of the present disclosure, when the aqueous solution is prepared by including sodium hydroxide as a basic material and adding sodium hyaluronate thereto, the aqueous solution may include 0.2 M or more of sodium ions.

In exemplary embodiments of the present disclosure, the aqueous solution may further include a crosslinking agent. The crosslinking agent, which is a compound having one or more functional groups, may be specifically a compound having one or more aldehyde groups, carbodiimide, epoxy groups, or vinyl sulfone groups. More specifically, the crosslinking agent may be a compound having two or more epoxy groups or divinyl sulfone. For example, the crosslinking agent may be 1-ethyl-3-(3-dimethylaminopropyl)carbodiimide hydrochloride (EDCl·HCl), 1-cyclohexyl-3-(2-morpholinoethyl)carbodiimide-metho-p-toluenesulfonate, 1-cyclohexyl-3-(2-morpholinoethyl)carbodiimide hydrochloride, glutaraldehyde, divinyl sulfone, 1,4-butanediol diglycidyl ether (BDDE), ethylene glycol diglycidyl ether (EGDGE), 1,6-hexanediol diglycidyl ether, propylene glycol diglycidyl ether, polypropylene glycol diglycidyl ether, polytetramethylene glycol diglycidyl ether, neopentyl glycol diglycidyl ether, polyglycerol polyglycidyl ether, diglycerol polyglycidyl ether, glycerol polyglycidyl ether, tri-methylpropane polyglycidyl ether, 1,2-(bis(2,3-epoxypropoxy)ethylene, pentaerythritol polyglycidyl ether, sorbitol polyglycidyl ether, or a mixture thereof, and in one specific embodiment, the crosslinking agent may be butanediol diglycidyl ether, divinyl sulfone, or a mixture thereof. In one specific embodiment, the crosslinking agent may be butanediol diglycidyl ether (BDDE). In one specific embodiment, the crosslinking agent may be divinyl sulfone (DVS).

In exemplary embodiments of the present disclosure, the aqueous solution may include the crosslinking agent in an amount of 0.005 mol to 1 mol, and specifically, 0.01 mol to 0.8 mol with respect to 1 mol of hyaluronic acid, a salt thereof, or a mixture thereof.

In exemplary embodiments of the present disclosure, the aqueous solution may include the crosslinking agent in an amount of about 10 μl to about 500 μl, and specifically, about 50 μl to about 400 μl with respect to 1 g of hyaluronic acid, a salt thereof, or a mixture thereof.

In exemplary embodiments of the present disclosure, in preparing the mixed solution including the solid hyaluronic acid particles by adding ethanol to the aqueous solution, the ethanol may be added in a volume of about 1 volume to about 10 volumes with respect to 1 volume of the aqueous solution including hyaluronic acid, a salt thereof or a mixture thereof. Specifically, when the mixed solution is prepared, a volume ratio of the aqueous solution and ethanol added thereto may be about 1:about 1 to about 10, and more specifically about 1:about 2 to about 8. When ethanol is added within the above range, the hyaluronic acid gel prepared by using the solid hyaluronic acid particles may exhibit excellent rheological properties and may exhibit excellent effects on the treatment or prevention of arthritis.

In exemplary embodiments of the present disclosure, when ethanol is added to the aqueous solution including hyaluronic acid, a salt thereof, or a mixture thereof, the ethanol addition rate may be constant or may vary. Specifically, the ethanol addition rate may be constant.

In exemplary embodiments of the present disclosure, during the process of adding ethanol to the aqueous solution including hyaluronic acid, a salt thereof, or a mixture thereof, the mixed solution of the aqueous solution and ethanol may be continuously stirred. Specifically, during the process of adding ethanol, the mixed solution may be stirred at about 50 rpm to about 300 rpm, and more specifically, about 50 rpm to about 250 rpm.

In exemplary embodiments of the present disclosure, the stirring speed of the mixed solution may be constant or may vary. Specifically, the stirring speed of the mixed solution may be constant.

In exemplary embodiments of the present disclosure, when ethanol is added to the aqueous solution, the ethanol may be slowly added over a predetermined time. Hyaluronic acid, which is a linear polymer, is extracted in the form of a thread (a ball of thread), when dehydrated by ethanol. Specifically, ethanol may be slowly added to the aqueous solution such that a fibrous (a ball of thread) hyaluronic acid solid or a lump of hyaluronic acid solid is not produced. More specifically, ethanol may be slowly added to the aqueous solution such that hyaluronic acid is precipitated in the form of fine particles, like powder. When the ethanol addition rate exceeds the following range, hyaluronic acid is extracted in the form of fibers, and thus pH control is not possible during washing, and washing is not easy, and the final product is browned or viscoelasticity is lowered to produce hyaluronic acid in a liquid state. When ethanol is added to the aqueous solution, the ethanol addition rate may be about 20 mL/min to about 1000 mL/min. Specifically, the ethanol addition rate may be about 20 mL/min to about 700 mL/min, and more specifically, the ethanol addition rate may be about 20 mL/min to about 500 mL/min. When ethanol is added at the above rate, hyaluronic acid does not agglomerate and may be precipitated in the form of fine particles, like powder.

In exemplary embodiments of the present disclosure, when ethanol is added, the rate of volume change of ethanol with respect to the volume of the mixed solution including the hyaluronic acid-containing aqueous solution and ethanol may be 0.5% (v/v)/min to 35% (v/v)/min.

As described, when ethanol is slowly added over a predetermined time, hyaluronic acid particles may be precipitated in the form of uniform fine particles.

Further, it is possible to wash the hyaluronic acid obtained in the form of uniform fine particles with ethanol or a solution containing ethanol after the crosslinking reaction, and a phenomenon, in which the crosslinked hyaluronic acid product in the form of powder swell, may hardly occur or may be minimized during washing. Therefore, during washing the crosslinking agent or impurities, sufficient washing is possible with a small amount of a washing solution, and mass-production is possible with economic efficiency, because uniformity of the properties of the crosslinked hyaluronic acid product may be improved.

In exemplary embodiments of the present disclosure, the solid hyaluronic acid particles and the crosslinking agent may react with each other to proceed a crosslinking reaction, and a crosslinked hyaluronic acid product in the form of powder, which is fine particles, may be produced by the crosslinking reaction. The crosslinked hyaluronic acid product in the form of powder, which is fine particles, may have a uniform particle size and may have a uniform degree of crosslinking.

In exemplary embodiments of the present disclosure, the crosslinking reaction between the solid hyaluronic acid particles and the crosslinking agent may be performed at about 20° C. to about 40° C. for about 6 hours to about 24 hours. The degradation of hyaluronic acid may be minimized under the above reaction conditions, and thus a crosslinked hyaluronic acid product having a long chain length may be produced. In addition, a crosslinked hyaluronic acid product exhibiting a degree of crosslinking suitable for treating arthritis and having excellent physical properties may be produced.

In exemplary embodiments of the present disclosure, the crosslinked hyaluronic acid product in the form of fine powder may have D90 of about 80 μm or less.

In exemplary embodiments of the present disclosure, the crosslinked hyaluronic acid product in the form of uniform fine powder may have D10 of about 2.5 μm to about 6 μm, D50 of about 8 μm to about 20 μm, and D90 of about 25 μm to about 80 μm.

In exemplary embodiments of the present disclosure, the particle size of the crosslinked hyaluronic acid product in the form of fine powder may be measured by laser particle size analysis, and specifically, by a dry method.

In exemplary embodiments of the present disclosure, the crosslinked hyaluronic acid product in the form of powder may be amorphous, and its X-ray powder diffraction analysis pattern may exhibit a halo pattern. Specifically, the crosslinked hyaluronic acid product in the form of powder may exhibit an X-ray powder diffraction pattern (XRD) as in FIG. 3.

In exemplary embodiments of the present disclosure, the crosslinked hyaluronic acid product in the form of powder may be amorphous, and particles of the crosslinked product may have D10 of about 2.5 μm to about 6 μm, D50 of about 8 μm to about 20 μm, and D90 of about 25 μm to about 80 μm.

In exemplary embodiments of the present disclosure, after performing the crosslinking reaction, pH of the mixed solution may be adjusted to less than 9 to terminate the crosslinking reaction. For example, after performing the crosslinking reaction, pH of the mixed solution may be adjusted to 6 or more and less than 9 by adding hydrochloric acid (HCl) to terminate the crosslinking reaction.

In exemplary embodiments of the present disclosure, after terminating the crosslinking reaction, the crosslinked hyaluronic acid product in the form of powder, which is fine particles, may be obtained by filtration. In other words, since the crosslinked hyaluronic acid product in the form of powder of the present disclosure has a powder form, it sinks in the solution when not stirred, and may be easily obtained by separating the crosslinked hyaluronic acid product in the form of powder from the liquid through a simple filtration process.

In exemplary embodiments of the present disclosure, the method may further include washing the crosslinked hyaluronic acid product in the form of powder. By the washing, the crosslinking agent and impurities that remain in the crosslinked hyaluronic acid product in the form of powder may be removed. The washing may be performed once or more using ethanol or a solution containing ethanol, and for example, the washing may be performed several times using about 70% (w/w), about 95% (w/w) of an aqueous ethanol solution. For example, the obtained crosslinked hyaluronic acid product in the form of powder may be washed three times to five times while exchanging about 70% (w/w) and about 95% (w/w) of an aqueous ethanol solution with each other.

In exemplary embodiments of the present disclosure, the washing may be performed under a condition of less than pH 9, and specifically, may be performed under a condition of pH 6 to less than pH 9.

In the washing of the present disclosure, as compared with common methods, ethanol or a solution containing ethanol such as an aqueous ethanol solution, rather than an aqueous buffer solution such as pure water or a phosphate buffer, is used, thereby inhibiting a phenomenon in which the crosslinked hyaluronic acid product swells during washing. Thus, quality control is easy. Since swelling hardly occurs or is minimized during washing, the crosslinking agent and impurities may be sufficiently removed with a small amount of the washing solution, and mass-production may be easily performed.

In exemplary embodiments of the present disclosure, the method may further include drying the crosslinked hyaluronic acid product in the form of powder, after washing. The drying may be vacuum drying, and may be performed at about 35° C. to about 70° C. for about 10 hours to 40 hours.

The present disclosure provides a crosslinked hyaluronic acid product in the form of powder, which is prepared by a method including:
preparing an aqueous solution including hyaluronic acid, a salt thereof, or a mixture thereof;
adding a crosslinking agent to the aqueous solution to cause a crosslinking reaction of the hyaluronic acid to occur; and
adding ethanol to the aqueous solution to solidify the hyaluronic acid into particles,
wherein ethanol is slowly added to the aqueous solution over a predetermined time.

The method may further include causing a crosslinking reaction of an aqueous solution including the hyaluronic acid particles to occur. The reaction may be to maintain the crosslinking reaction of the aqueous solution including hyaluronic acid particles.

The crosslinked hyaluronic acid product in the form of powder prepared by the above method, which is fine particles, is easy to handle and has a uniform degree of crosslinking. Further, since it does not swell during the washing and maintains the form of fine particles like powder, washing is easy and mass production is possible.

Further, during the washing, it is easy to wash NaOH and the crosslinking agent such as unreacted BDDE from the crosslinked product in the form of powder, pH adjustment is possible, and subsequently, appropriate viscoelasticity of the final gel may be induced, and the browning reaction, which is denaturation of the crosslinked hyaluronic acid product according to pH, may be minimized and suppressed.

The particle size distribution of the crosslinked hyaluronic acid product in the form of powder of the present disclosure may exhibit a particle size distribution D90 of about 80 μm or less.

The crosslinked hyaluronic acid product in the form of uniform fine powder of the present disclosure may exhibit particle size distributions D10 of about 2.5 μm to about 6 μm, D50 of about 8 μm to about 20 μm, and D90 of about 25 μm to about 80 μm.

In exemplary embodiments of the present disclosure, the particle size of the crosslinked hyaluronic acid product in the form of fine powder may be measured by laser particle size analysis, and specifically, by a dry method.

The crosslinked hyaluronic acid product in the form of powder of the present disclosure may be amorphous, and its X-ray powder diffraction analysis pattern may exhibit a halo pattern. Specifically, the crosslinked hyaluronic acid product in the form of powder may exhibit an X-ray powder diffraction pattern (XRD) as in FIG. 3.

A method of preparing the crosslinked hyaluronic acid product in the form of powder and physical properties of the crosslinked hyaluronic acid product are the same as described above.

The present disclosure provides a method of preparing a crosslinked hyaluronic acid hydrogel exhibiting excellent rheological properties, which is used to easily remove foreign substances, is economical, and is optimized for mass production.

The method of preparing a crosslinked hyaluronic acid hydrogel of the present disclosure includes:
  preparing an aqueous solution including hyaluronic acid, a salt thereof, or a mixture thereof;
  adding a crosslinking agent to the aqueous solution to cause a crosslinking reaction of the hyaluronic acid to occur;
  adding ethanol to the aqueous solution to solidify the hyaluronic acid into particles;
  maintaining the crosslinking reaction of the aqueous solution including the hyaluronic acid particles to prepare a crosslinked hyaluronic acid product in the form of powder; and
  hydrating the crosslinked hyaluronic acid product in the form of powder.

With regard to the method, when ethanol is added to the aqueous solution, the ethanol may be slowly added to the aqueous solution over a predetermined time.

A method of preparing the crosslinked hyaluronic acid product in the form of powder and physical properties of the crosslinked hyaluronic acid product are the same as described above.

The crosslinked hyaluronic acid hydrogel prepared according to the preparation method of the present disclosure may exhibit rheological properties optimized for the prevention or treatment of arthritis. Further, since it is possible to filter the crosslinked hyaluronic acid hydrogel using a filter, foreign substances are easily removed, and thus impurity management is easy, when formulated into a drug, and thus it has remarkably excellent advantages in terms of economic efficiency and mass production. Further, the crosslinked hyaluronic acid hydrogel has excellent quality uniformity, and rheological properties of the crosslinked hyaluronic acid gels prepared according to each batch are almost equal to each other, indicating uniform physical properties and excellent reproducibility.

In exemplary embodiments of the present disclosure, the elasticity (storage modulus, G') and viscosity (loss modulus, G") of the crosslinked hyaluronic acid hydrogel may exhibit a range suitable for use as a human joint supplement.

The crosslinked hyaluronic acid hydrogel may exhibit elasticity of about 30 Pa to about 200 Pa and viscosity of about 10 Pa to about 100 Pa, and specifically, elasticity of about 100 Pa to about 150 Pa and viscosity of about 10 Pa to about 60 Pa. The crosslinked hyaluronic acid hydrogel of the present disclosure may exhibit elasticity of about 30 Pa to about 200 Pa and viscosity of about 10 Pa to about 100 Pa, and a filtration process thereof using a filter is possible.

The crosslinked hyaluronic acid hydrogel of the present disclosure may exhibit elasticity of about 30 Pa to about 200 Pa and viscosity of about 10 Pa to about 100 Pa, a particle size of D90 of 240 μm or less, more specifically, particle size distributions D10 of about 25 μm to about 40 μm, D50 of about 70 μm to about 110 μm, and D90 of about 190 μm to about 240 μm, or particle size distributions D10 of about 10 μm to about 30 μm, D50 of about 35 μm to about 65 μm, and D90 of about 80 μm to about 120 μm, and a filtration process thereof using a filter is possible.

With regard to the method of preparing the crosslinked hyaluronic acid hydrogel, the preparation of the crosslinked hyaluronic acid product in the form of powder is the same as described above.

In exemplary embodiments of the present disclosure, the hydration of the crosslinked hyaluronic acid product in the form of powder may be mixing the crosslinked hyaluronic acid product in the form of powder with water or a solution comprising water. Here, the solution comprising water may be a buffer solution, and specifically, a phosphate buffer solution.

The crosslinked hyaluronic acid product in the form of powder may be added at a concentration of about 5 mg/mL to about 15 mg/mL with respect to water or the solution comprising water. When the crosslinked hyaluronic acid product in the form of powder may be added at the above concentration to water or the solution comprising water, the crosslinked hyaluronic acid gel may exhibit viscosity and elasticity suitable for the treatment of arthritis, and may exhibit rheological properties at a filterable degree, and thus it is easy to remove foreign substances, and accordingly, quality control is easy, and the gel may exhibit an appropriate injection pressure when is filled into a syringe.

In exemplary embodiments of the present disclosure, the method may further include homogenizing the crosslinked hyaluronic acid hydrogel. The homogenizing may be performed using a homogenizer, and the crosslinked hyaluronic acid hydrogel may be homogenized using a homogenizer at about 7000 rpm or less, for example, at about 2000 rpm to about 7000 rpm for about 3 minutes to about 20 minutes.

In exemplary embodiments of the present disclosure, the method may further include filtering the crosslinked hyaluronic acid hydrogel using a filter with a pore size of about 5 μm to about 30 μm. Since the crosslinked hyaluronic acid hydrogel may be filtered through a filter having a small pore size, foreign substances may be easily removed from the hyaluronic acid hydrogel, and thus quality control is easy, and the risk of containing foreign substances may be reduced, and physical characteristics of the hydrogel may be maintained without great changes, and uniformity of the particle size and particle size distribution may be improved, leading to high quality improvement.

In exemplary embodiments of the present disclosure, filtration using the filter may be performed under reduced pressure or vacuum, and specifically, may be performed under a pressure of about 80 kPa to about 20 kPa.

In exemplary embodiments of the present disclosure, the filtration using the filter may be performed once or more, and specifically, may be performed once or twice. Even though the frequency of the filtration process through the filter is increased, the properties of the hyaluronic acid hydrogel may be equally maintained, and the particle size may be reduced.

In exemplary embodiments of the present disclosure, the hyaluronic acid hydrogel before the filtration process through the filter may exhibit a particle size distribution D90 of about 240 μm or less.

In exemplary embodiments of the present disclosure, the hyaluronic acid hydrogel before the filtration process through the filter may exhibit particle size distributions D10 of about 25 μm to about 40 μm, D50 of about 70 μm to about 110 μm, and D90 of about 190 μm to about 240 μm.

In exemplary embodiments of the present disclosure, the crosslinked hyaluronic acid hydrogel before the filtration process through the filter may be amorphous, and its X-ray powder diffraction analysis pattern may exhibit a halo pattern. Specifically, the hyaluronic acid hydrogel may exhibit an X-ray powder diffraction pattern (XRD) as in FIG. 4.

Figure 4:
FIG. 4 shows results of X-ray powder diffraction analysis of a crosslinked hyaluronic acid hydrogel in the form of powder according to Example 6, wherein the vertical axis represents intensity (cps), and the horizontal axis represents 2θ(°)

The crosslinked hyaluronic acid hydrogel of the present disclosure may be amorphous, may exhibit the X-ray powder diffraction pattern (XRD) as in FIG. 4, and may exhibit a particle size distribution D90 of 240 μm or less, and more specifically, particle size distributions D10 of about 25 μm to about 40 μm, D50 of about 70 μm to about 110 μm, and D90 of about 190 μm to about 240 μm. It is possible to perform the filtration process of the crosslinked hyaluronic acid hydrogel through the filter.

In exemplary embodiments of the present disclosure, the crosslinked hyaluronic acid hydrogel after the filtration process through the filter may exhibit a particle size distribution D90 of about 120 μm or less.

In exemplary embodiments of the present disclosure, the hyaluronic acid hydrogel after the filtration process through the filter may exhibit particle size distributions D10 of about 10 μm to about 30 μm, D50 of about 35 μm to about 65 μm, and D90 of about 80 μm to about 120 μm.

In exemplary embodiments of the present disclosure, the crosslinked hyaluronic acid hydrogel after the filtration process through the filter may be amorphous, and its X-ray powder diffraction analysis pattern may exhibit a halo pattern. Specifically, the hyaluronic acid hydrogel may exhibit an X-ray powder diffraction pattern (XRD) as in FIG. 5.

Figure 5:
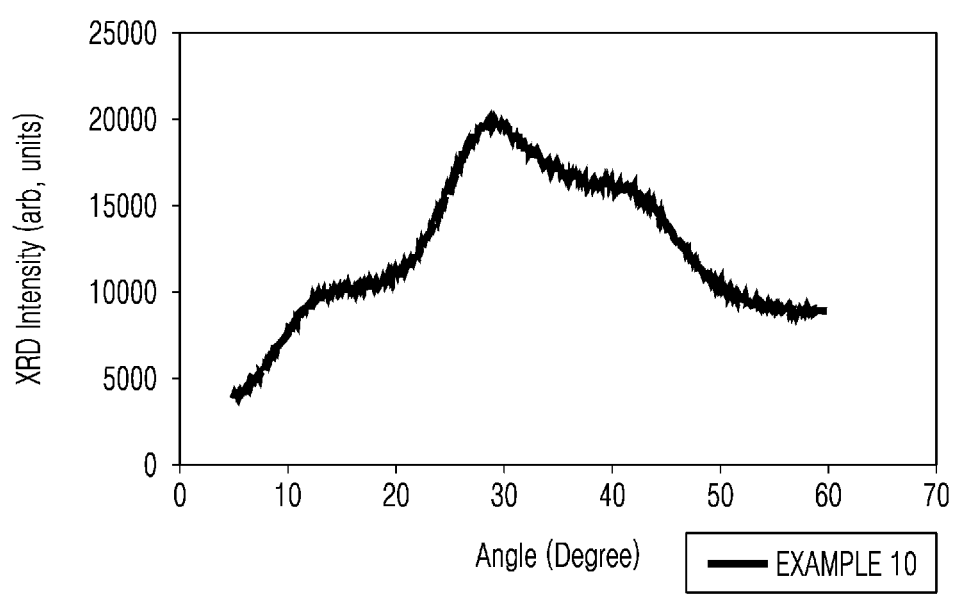
FIG. 5 shows results of X-ray powder diffraction analysis of a crosslinked hyaluronic acid hydrogel after filtration according to Example 10, wherein the vertical axis represents intensity (cps), and the horizontal axis represents 2θ(°)
Figure 6:
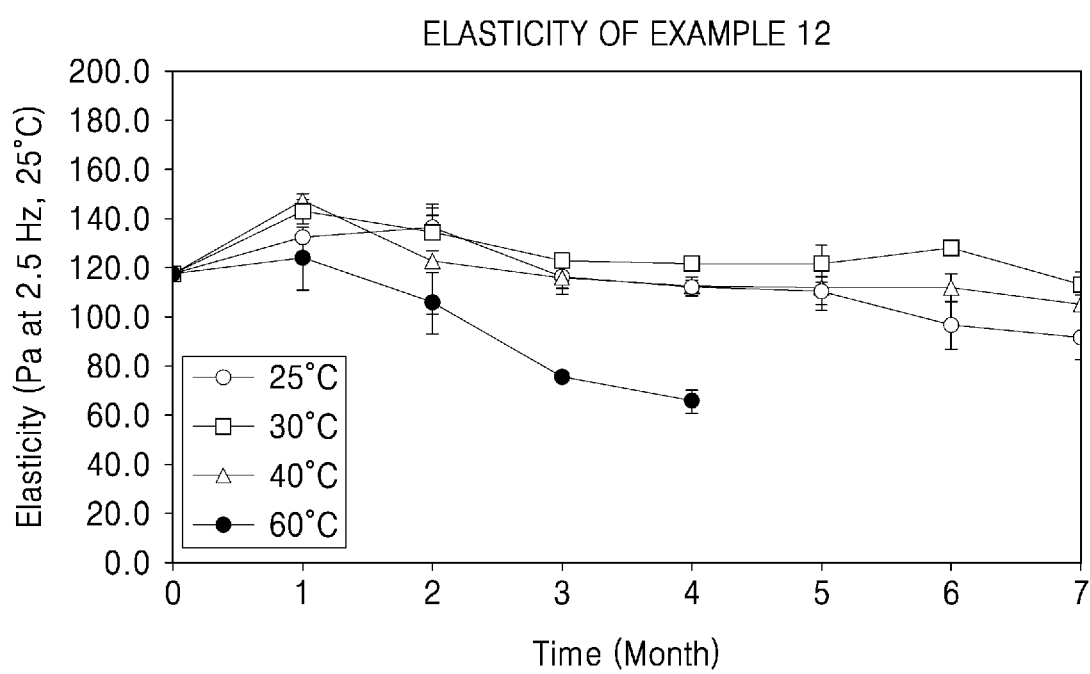
FIG. 6 shows elasticity (Pa at 2.5 Hz, 25° C.) according to time and temperature changes, measured for a hyaluronic acid hydrogel according to Example 12.
Figure 7:
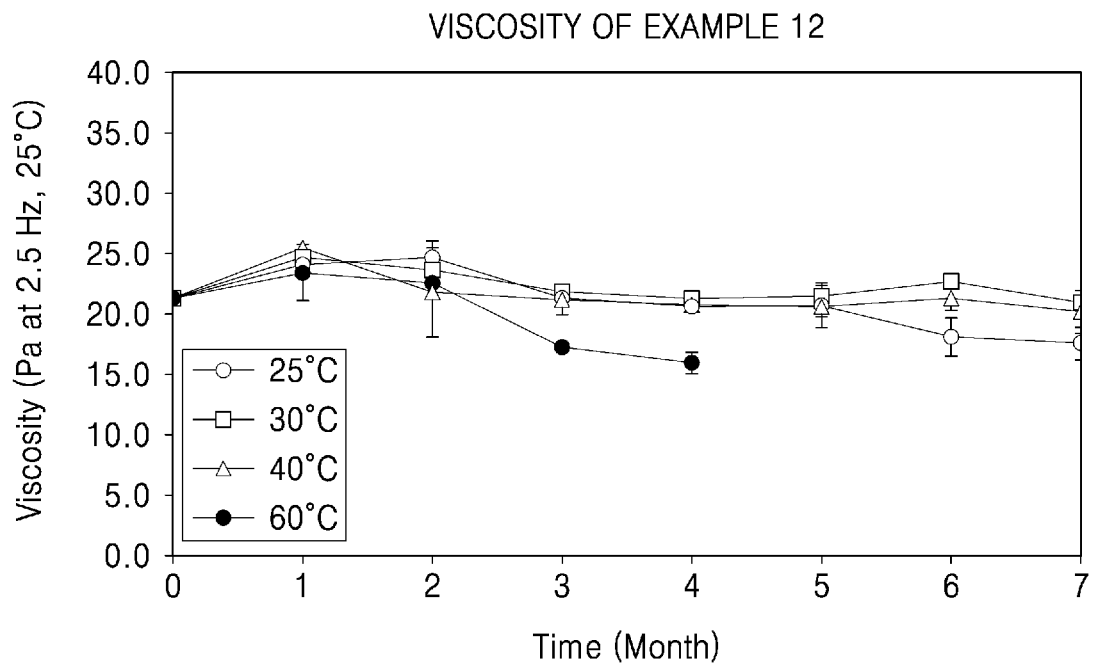
FIG. 7 shows viscosity (Pa at 2.5 Hz, 25° C.) according to time and temperature changes, measured for the hyaluronic acid hydrogel according to Example 12.
Figure 8:
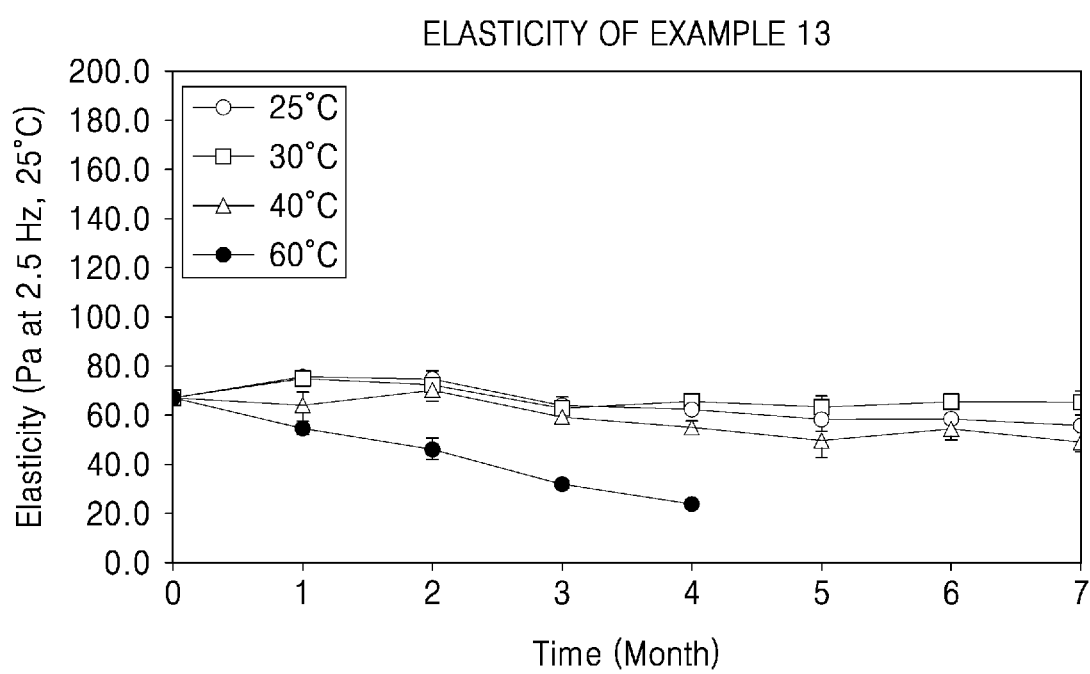
FIG. 8 shows elasticity (Pa at 2.5 Hz, 25° C.) according to time and temperature changes, measured for a hyaluronic acid hydrogel according to Example 13.
Figure 9:
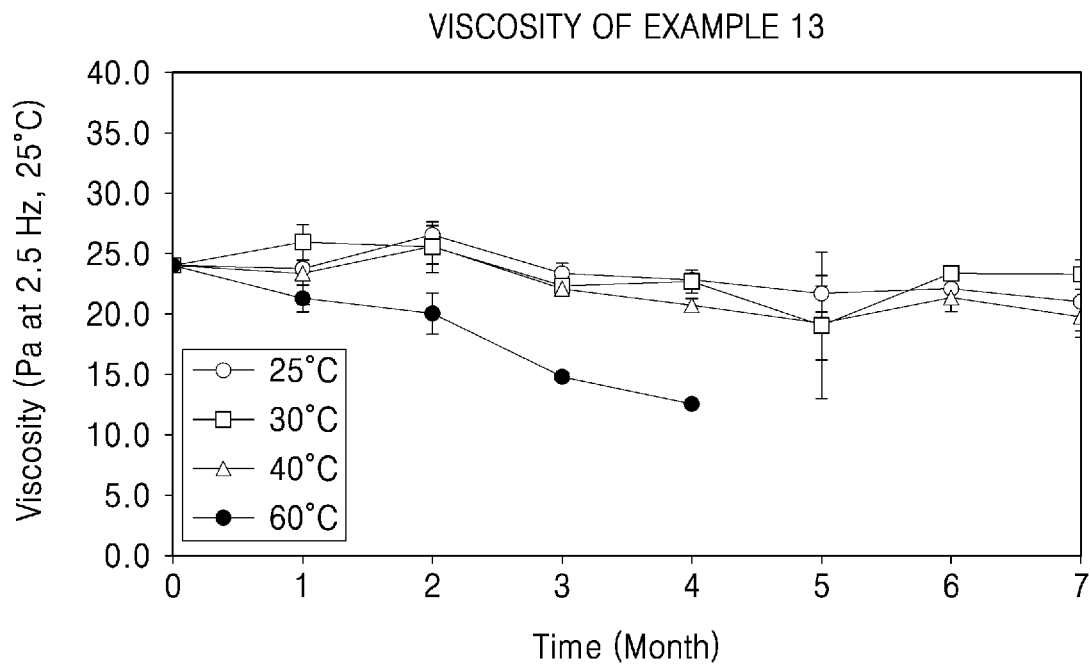
FIG. 9 shows viscosity (Pa at 2.5 Hz, 25° C.) according to time and temperature changes, measured for the hyaluronic acid hydrogel according to Example 13.
Figure 10:
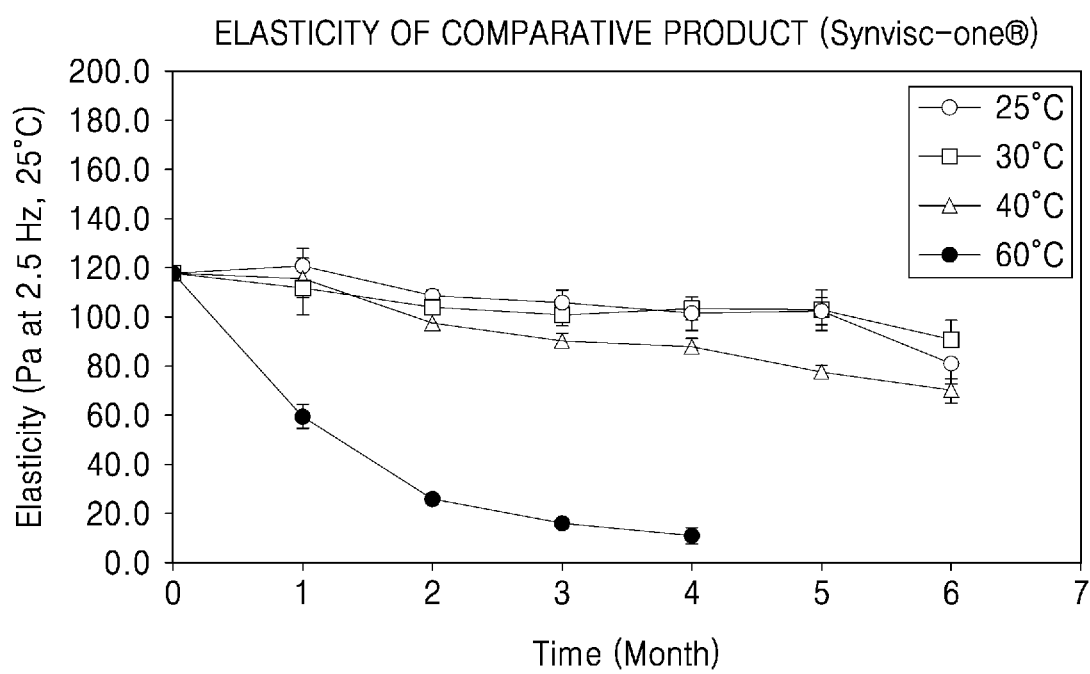
FIG. 10 shows elasticity (Pa at 2.5 Hz, 25° C.) according to time and temperature changes, measured for a comparative product (SYNVISC-ONE®)
Figure 11:
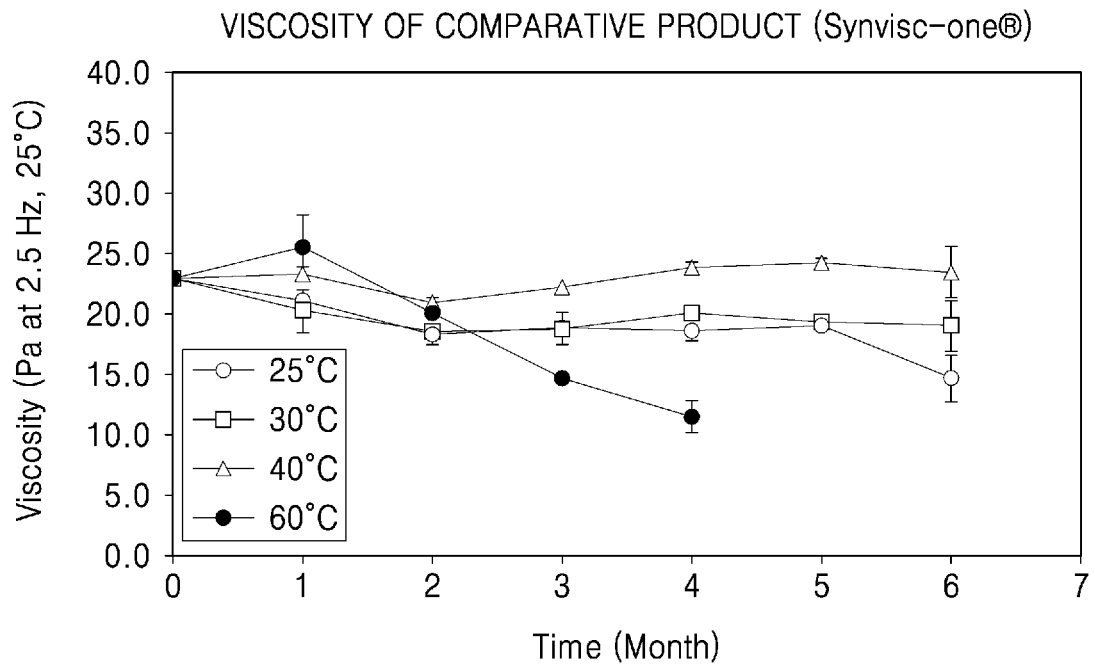
FIG. 11 shows viscosity (Pa at 2.5 Hz, 25° C.) according to time and temperature changes, measured for the comparative product (SYNVISC-ONE®).

The crosslinked hyaluronic acid hydrogel of the present disclosure may be amorphous, may exhibit the X-ray powder diffraction pattern (XRD) as in FIG. 5, and may exhibit a particle size distribution D90 of 120 μm or less, and more specifically, particle size distributions D10 of about 10 μm to about 30 μm, D50 of about 35 μm to about 65 μm, and D90 of about 80 μm to about 120 μm. It is possible to perform the filtration process of the crosslinked hyaluronic acid hydrogel through the filter.

In the present disclosure, the particle size of the crosslinked hyaluronic acid hydrogel may be measured by laser particle size analysis.

In the present disclosure, the particle size of the crosslinked hyaluronic acid hydrogel may be measured by a wet method.

In exemplary embodiments of the present disclosure, the filtration may be performed after homogenizing.

In exemplary embodiments of the present disclosure, the method may further include sterilizing the crosslinked hyaluronic acid hydrogel. The sterilizing may be performed at about 100° C. or higher for about 10 minutes or longer, and specifically, at about 121° C. or higher for about 15 minutes or longer.

In exemplary embodiments of the present disclosure, the sterilizing may be performed before or after filling the crosslinked hyaluronic acid hydrogel into a syringe, and specifically, after filling the crosslinked hyaluronic acid gel into a syringe.

The present disclosure provides a crosslinked hyaluronic acid hydrogel which is prepared by a method including:
  preparing an aqueous solution including hyaluronic acid, a salt thereof, or a mixture thereof;
  adding a crosslinking agent to the aqueous solution to cause a crosslinking reaction of the hyaluronic acid to occur;
  adding ethanol to the aqueous solution to solidify the hyaluronic acid into particles;
  maintaining the crosslinking reaction of the aqueous solution including the hyaluronic acid particles to prepare a crosslinked hyaluronic acid product in the form of powder; and
  hydrating the crosslinked hyaluronic acid product in the form of powder.

With regard to the method, when ethanol is added to the aqueous solution, the ethanol is slowly added to the aqueous solution over a predetermined time.

The hyaluronic acid hydrogel may exhibit rheological properties optimized for the alleviation, prevention, or treatment of pain caused by degenerative arthritis. Further, since it is possible to filter the crosslinked hyaluronic acid hydrogel using a filter with a small pore size, foreign substances are easily removed, and thus impurity management is easy, when formulated into a drug and a medical device, and thus it has remarkably excellent advantages in terms of economic efficiency and mass production. Further, the crosslinked hyaluronic acid hydrogel has excellent quality uniformity, and rheological properties of the crosslinked hyaluronic acid hydrogels prepared according to each batch are almost equal to each other, indicating uniform physical properties and excellent reproducibility.

The crosslinked hyaluronic acid hydrogel of the present disclosure may exhibit a particle size distribution D90 of about 240 μm or less.

The crosslinked hyaluronic acid hydrogel of the present disclosure may exhibit particle size distributions D10 of about 25 μm to about 40 μm, D50 of about 70 μm to about 110 μm, and D90 of about 190 μm to about 240 μm.

The crosslinked hyaluronic acid hydrogel of the present disclosure may be amorphous, and its X-ray powder diffraction analysis pattern may exhibit a halo pattern. Specifically, the hyaluronic acid hydrogel may exhibit an X-ray powder diffraction pattern (XRD) as in FIG. 4.

According to exemplary embodiments of the present disclosure, the crosslinked hyaluronic acid hydrogel may be filtered using a filter with a pore size of about 5 μm to about 30 μm.

The crosslinked hyaluronic acid hydrogel after filtration of the present disclosure may exhibit a particle size distribution D90 of about 120 μm or less.

The crosslinked hyaluronic acid hydrogel after filtration of the present disclosure may exhibit particle size distributions D10 of about 10 μm to about 30 μm, D50 of about 35 μm to about 65 μm, and D90 of about 80 μm to about 120 μm.

The crosslinked hyaluronic acid hydrogel after filtration of the present disclosure may be amorphous, and its X-ray powder diffraction analysis pattern may exhibit a halo pattern. Specifically, the hyaluronic acid hydrogel after filtration may exhibit an X-ray powder diffraction pattern (XRD) as in FIG. 5.

In the present disclosure, a method of preparing the crosslinked hyaluronic acid product particles in the form of powder and the crosslinked hyaluronic acid hydrogel, and physical properties of the crosslinked hyaluronic acid product particles in the form of powder and physical properties of the crosslinked hyaluronic acid hydrogel are the same as described above.

In exemplary embodiments of the present disclosure, the hyaluronic acid hydrogel obtained by the filtration may have elasticity of 30 Pa to 200 Pa and viscosity of 10 Pa to 100 Pa, and specifically, elasticity of 100 Pa to 150 Pa and viscosity of 10 Pa to 60 Pa.

The present disclosure provides a syringe filled with the crosslinked hyaluronic acid hydrogel. When the syringe is applied to the human body, it may exhibit a pressure suitable for injection, and may exhibit excellent effects of alleviating, preventing, and treating degenerative arthritis due to the excellent rheological properties of the crosslinked hyaluronic acid gel.

EXAMPLE

Hereinafter, the present disclosure will be described in more detail with reference to the following exemplary embodiments. However, the following exemplary embodiments are only for illustrating the present disclosure, and the scope of the present disclosure is not limited thereto.

Example 1

Example 1-1

0.2 M to 0.3 M of an aqueous NaOH solution (pH>9) was mixed with butanediol diglycidyl ether (BDDE), and a reaction product was prepared such that a concentration of sodium hyaluronate (Na-HA, molecular weight: 1.0 MDa to 4.0 MDa) was 2% (w/v). In this regard, a ratio of BDDE and sodium hyaluronate was 100 µl (BDDE)/1 g (HA).

This reaction product was stirred at room temperature to dissolve sodium hyaluronate, and thus 250 mL of a sodium hyaluronate-containing aqueous solution (Na-HA solution) was prepared and stirred at 25° C. to 35° C. for 4 hours to 6 hours at 250 rpm to cause a crosslinking reaction to occur. Ethanol was added to the sodium hyaluronate-containing aqueous solution until a volume ratio of the sodium hyaluronate-containing aqueous solution and ethanol was 1:5, and at this time, ethanol was added at a rate of 20 mL/min to prevent agglomeration of sodium hyaluronate.

Sodium hyaluronate was precipitated in the form of powder, and then stirred at 25° C. for 24 hours or shorter at 250 rpm to cause a crosslinking reaction to occur. After the crosslinking reaction, 2.0 M or less of HCl solution was added to adjust pH (pH 6.0 to less than 9.0), and thus the reaction was terminated. The solidified crosslinked hyaluronic acid product was recovered through filtering. The solidified crosslinked hyaluronic acid product was washed several times while alternatively exchanging 95% (w/w) ethanol and 70% (w/w) ethanol. After washing, the recovered crosslinked hyaluronic acid was dried under vacuum at 60° C. or lower for 24 hours or shorter to remove ethanol and water, thereby obtaining the crosslinked hyaluronic acid product in the form of powder.

Example 1-2

A crosslinked hyaluronic acid product in the form of powder was obtained in the same manner as in Example 1-1, except that ethanol was added to the sodium hyaluronate-containing aqueous solution at a rate of 80 mL/min.

Example 1-3

A crosslinked hyaluronic acid product in the form of powder was obtained in the same manner as in Example 1-1, except that ethanol was added to the sodium hyaluronate-containing aqueous solution at a rate of 200 mL/min.

Example 2

A crosslinked hyaluronic acid product in the form of powder was prepared in the same manner as in Example 1-1, except that ethanol was added to the sodium hyaluronate-containing aqueous solution until a volume ratio of the sodium hyaluronate-containing aqueous solution and ethanol was 1:3.

Example 3

A crosslinked hyaluronic acid product in the form of powder was prepared in the same manner as in Example 1-1, except that ethanol was added to the sodium hyaluronate-containing aqueous solution until a volume ratio of the sodium hyaluronate-containing aqueous solution and ethanol was 1:7.

Example 4

A crosslinked hyaluronic acid product in the form of powder was prepared in the same manner as in Example 1-1, except that DVS instead of BDDE was added as a crosslinking agent at 100 µl (DVS)/1 g(HA), ethanol was added to the sodium hyaluronate-containing aqueous solution until a volume ratio of the sodium hyaluronate-containing aqueous solution and ethanol was 1:3.

Example 5

The crosslinked hyaluronic acid product in the form of powder, which was prepared in Example 1-1, was added to phosphate buffered saline (PBS) at 10 mg/mL to 15 mg/mL to obtain a hydrogel. The hydrogel was homogenized using a homogenizer at 7000 rpm or less. The homogenized gel was sterilized at 121° C. for 20 minutes or shorter to obtain a crosslinked hyaluronic acid hydrogel.

Example 6

The crosslinked hyaluronic acid product in the form of powder, which was prepared in Example 2, was dissolved in PBS at 10 mg/mL to 15 mg/mL to obtain a hydrogel. The hydrogel was homogenized using a homogenizer at 7000 rpm or less. The homogenized gel was sterilized at 121° C. for 20 minutes or shorter to obtain a crosslinked hyaluronic acid hydrogel.

Example 7

The crosslinked hyaluronic acid product in the form of powder, which was prepared in Example 3, was dissolved in PBS at 10 mg/mL to 15 mg/mL to obtain a hydrogel. The hydrogel was homogenized using a homogenizer at 7000 rpm or less. The homogenized gel was sterilized at 121° C. for 20 minutes or shorter to obtain a crosslinked hyaluronic acid hydrogel.

Example 8

The crosslinked hyaluronic acid product in the form of powder, which was prepared in Example 4, was dissolved in PBS at 10 mg/mL to 15 mg/mL to obtain a hydrogel. The hydrogel was homogenized using a homogenizer at 7000 rpm or less. The homogenized gel was sterilized at 121° C. for 20 minutes or shorter to obtain a crosslinked hyaluronic acid hydrogel.

Example 9

The crosslinked hyaluronic acid product in the form of powder, which was prepared in Example 2, was dissolved in PBS at 6 mg/mL to 8 mg/mL to obtain a hydrogel. The hydrogel was homogenized using a homogenizer at 7000 rpm or less. The homogenized hydrogel was sterilized at 121° C. for 20 minutes or shorter to obtain a crosslinked hyaluronic acid gel.

Example 10

A crosslinked hyaluronic acid product in the form of powder was prepared in the same manner as in Example 2.

The prepared crosslinked hyaluronic acid product in the form of powder was dissolved in PBS at 10 mg/mL to 15 mg/mL to obtain a hydrogel. The gel was homogenized using a homogenizer at 7000 rpm or less. The homogenized hydrogel was filtered using a solid suspension filtering apparatus, with joint (S.S filtering apparatus) in a vacuum filtering apparatus, and at this time, Nylon filter paper of 25 µm or less was used as the filter, and filtration was performed at a pressure of about 80 kPa or less. The filtered hydrogel was sterilized for 20 minutes or shorter to obtain a crosslinked hyaluronic acid hydrogel.

Example 11

A crosslinked hyaluronic acid product in the form of powder was prepared in the same manner as in Example 2.

The prepared crosslinked hyaluronic acid product in the form of powder was dissolved in PBS at 10 mg/mL to 15 mg/mL to obtain a hydrogel. The homogenized hydrogel was serially filtered twice using a solid suspension filtering apparatus, with joint (S.S filtering apparatus) in a vacuum filtering apparatus, and at this time, Nylon filter paper of 25 µm or less was used as the filter, and filtration was performed at a pressure of about 80 kPa or less. The filtered hydrogel was sterilized at 121° C. for 20 minutes or shorter to obtain a crosslinked hyaluronic acid hydrogel.

Comparative Example 1

Sodium hyaluronate was added to 0.8(w/w) to 1.2% (w/w) of an aqueous sodium hydroxide solution containing ethanol at a ratio of 8% (w/w) to 12% (w/w) and completely dissolved, and then BDDE was added and mixed at a ratio of 50 µl to 100 µl/1 g of sodium hyaluronate. When the mixing was completed, a crosslinking reaction was performed at a reaction temperature of about 40° C. to about 50° C. for a reaction time of about 6 hours or shorter. The completely reacted crosslinked hyaluronic acid product in the form of hydrogel was dialyzed against PBS. The hydrogel obtained after dialysis was washed with distilled water to remove BDDE, and the neutralized hydrogel was extracted with 95% (w/w) of an aqueous ethanol solution to obtain a primary crosslinked hyaluronic acid product in the form of powder.

The primary crosslinked hyaluronic acid product was subjected to a secondary crosslinking reaction. The primary crosslinked hyaluronic acid product in the form of powder was mixed with 0.8% (w/w) to 1.2% (w/w) of an aqueous sodium hydroxide solution at a weight ratio of 1:4 to 6, and completely dissolved therein. BDDE was added to and mixed with the obtained reaction mixture at a ratio of 50 µl to 100 µl/1 g of the primary crosslinked product. When the mixing was completed, a crosslinking reaction was performed at a reaction temperature of about 40° C. to about 50° C. for about 12 hours or shorter. When the reaction was completed, the produced secondary crosslinked product was dialyzed against PBS for about 12 hours to about 24 hours. The particles obtained after dialysis was washed with distilled water to remove BDDE, and the neutralized hydrogel was extracted with 95% (w/w) of an aqueous ethanol solution to obtain a secondary crosslinked hyaluronic acid product in the form of powder.

The primary crosslinked hyaluronic acid product and the secondary crosslinked hyaluronic acid product were used to prepare each gel in PBS at a weight ratio of 9:1 at a final concentration of 2% (w/w), and a pulverization process was performed to pass the gel through a sieve with a mesh of 500 µm by applying a physical force to the gel, thereby obtaining a final crosslinked hyaluronic acid product.

Experimental Example 1: Measurement of Viscoelasticity of Hyaluronic Acid Hydrogel (1)

Viscoelasticity was measured for the crosslinked hyaluronic acid hydrogels prepared in Examples. Viscoelasticity was measured using a rotational rheometer, KINEXUS™ Pro Rheometer (Malvern, Worchestershire, UK).

For measurement of dynamic viscoelasticity, a geometry with a diameter of 20 mm was used, and a measurement distance (GAP) between the geometry and the plate was 0.5 mm, and the temperature was kept constant at 25° C. until the end of the analysis. Frequency oscillation was used as a control program, and a storage modulus (G') and a loss modulus (G") corresponding to 2.5 Hz were measured by setting the frequency range from 0.1 Hz to 10 Hz.

The results of measuring viscoelasticity of each hydrogel according to Examples are as in Table 1. In Table 1, elasticity represents storage modulus (G') and viscosity represents loss modulus (G").

TABLE 1

|  | EXAMPLE 5 | EXAMPLE 6 | EXAMPLE 7 | EXAMPLE 8 | EXAMPLE 9 | EXAMPLE 10 |
|---|---|---|---|---|---|---|
| ELASTICITY (G', Pa at 2.5 Hz) | 111 | 114 | 68 | 161 | 42 | 113 |
| VISCOSITY (G", Pa at 2.5 Hz) | 19 | 25 | 20 | 19 | 11 | 35 |

Experimental Example 2: Measurement of Viscoelasticity of Hyaluronic Acid Hydrogel (2)

Crosslinked hyaluronic acid hydrogels were prepared three times separately according to the methods of Example 10 and Comparative Example 1. Viscoelasticity was measured for each of the crosslinked hyaluronic acid hydrogels as in Experimental Example 1, and mean values thereof and standard deviation are shown in Table 2 below.

TABLE 2

|  | EXAMPLE 10 | COMPARATIVE EXAMPLE 1 |
|---|---|---|
| ELASTICITY (G', Pa at 2.5 Hz) | 108.6 ± 4.5 (RSD: 4.1%) | 105.6 ± 15.7 (RSD: 14%) |
| VISCOSITY (G", Pa at 2.5 Hz) | 34.6 ± 0.5 (RSD: 1.6%) | 51.6 ± 5.6 (RSD: 11%) |

As confirmed in Table 2, according to the method of Example 10, the elasticity and viscosity of the crosslinked hyaluronic acid hydrogel exhibited a considerably low standard deviation, indicating almost constant physical properties for each batch. In contrast, according to the method of Comparative Example 1, the elasticity and viscosity of the crosslinked hyaluronic acid gel exhibited a large difference between the preparations.

These results indicate that a crosslinked hyaluronic acid hydrogel having uniform physical properties may be prepared according to the present disclosure.

Experimental Example 3: Analysis of Particle Size of Crosslinked Hyaluronic Acid Product in Form of Powder Particle sizes of sodium hyaluronate in the form of powder (molecular weight: 1.0 MDa to 4.0 MDa) which is a raw material used in Example 1-1 to Example 1-3, and the crosslinked hyaluronic acid products in the form of powder according to Example 1-1 to Example 1-3 were analyzed using a particle size analyzer (Mastersizer 3000, Malvern, England) by a dry method, and the results are shown in FIG. 1 and Table 3.

TABLE 3

| ETHANOL ADDITION RATE | PARTICLE SIZE DISTRIBUTION ACCORDING TO RELATIVE CUMULATIVE AMOUNT | | |
|---|---|---|---|
|  | D10 (μm) | D50 (μm) | D90 (μm) |
| EXAMPLE 1-1 | 3.5 ± 0.4 | 10.9 ± 0.1 | 31.1 ± 0.5 |
| EXAMPLE 1-2 | 4.2 ± 0.0 | 14.9 ± 0.1 | 49.8 ± 0.8 |
| EXAMPLE 1-3 | 4.1 ± 0.0 | 15.4 ± 0.2 | 68.1 ± 3.4 |
| RAW MATERIAL | 17.9 ± 0.0 | 48.1 ± 0.0 | 148 ± 1.9 |

As confirmed in FIG. 1 and Table 3, the crosslinked hyaluronic acid products in the form of powder according to Example 1-1 to Example 1-3 were obtained as crosslinked products in the form of finer powder than the raw material sodium hyaluronate.

Further, as the ethanol addition rate increased, the particle size tended to increase, and D90 value in the particle size distribution increased.

Experimental Example 4: Analysis of Particle Size of Crosslinked Hyaluronic Acid Hydrogel Particle sizes of the crosslinked hyaluronic acid hydrogels of Example 6, Example 10, and Example 11 were analyzed using a particle size analyzer (Microtrac, Montgomeryville, PA) by a wet method, and the results are shown in FIG. 2 and Table 4.

TABLE 4

| FILTRATION PROCESS | PARTICLE SIZE DISTRIBUTION ACCORDING TO RELATIVE CUMULATIVE AMOUNT | | |
|---|---|---|---|
|  | D10 (μm) | D50 (μm) | D90 (μm) |
| EXAMPLE 6 | 34.6 | 90.4 | 207 |
| EXAMPLE 10 | 19.3 | 52.9 | 101.9 |
| EXAMPLE 11 | 17.7 | 50.6 | 92.7 |

Figure 2:
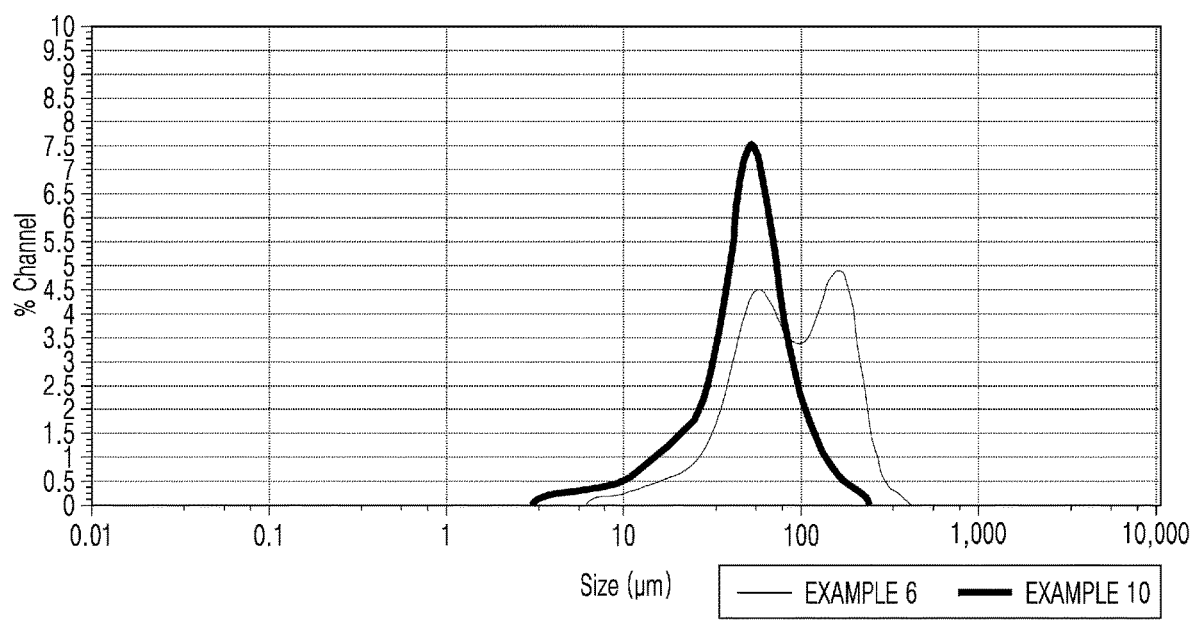
FIG. 2 shows particle size distributions of crosslinked hyaluronic acid hydrogels according to Example 6 and Example 10, wherein the vertical axis represents channel (%), and the horizontal axis represents particle size (μm)

According to FIG. 2 and Table 4, it was possible to filter the crosslinked hyaluronic acid hydrogels, and through the filtration, the particle size was decreased, and a more uniform particle size distribution was shown.

These results indicate that the crosslinked hyaluronic acid hydrogel was more homogenized through the filtration process, and thus uniformity of the particle size was improved.

Experimental Example 5: XRD Structural Analysis of Crosslinked Hyaluronic Acid Gel Physical properties of the crosslinked hyaluronic acid product in the form of powder according to Example 2 and the crosslinked hyaluronic acid hydrogels according to Examples 6 and 10 were examined by X-ray diffraction analysis. The peaks of the crystal structures were compared by a semi-quantitative (RIR) method by comparing the interplanar distance (d) and the relative reflectance intensity (I/Io) obtained from the measured XRD spectrum.

Instrument and conditions for the X-ray diffraction spectrum measurement are as follows.

<Method of Measuring X-Ray Powder Diffraction Spectrum>

Manufacturer: PANalytical (Almelo, Netherlands)
Model name: X'pert pro MPD
X-ray wavelength: 1.5405 Å of CuKγ

Figure 3:
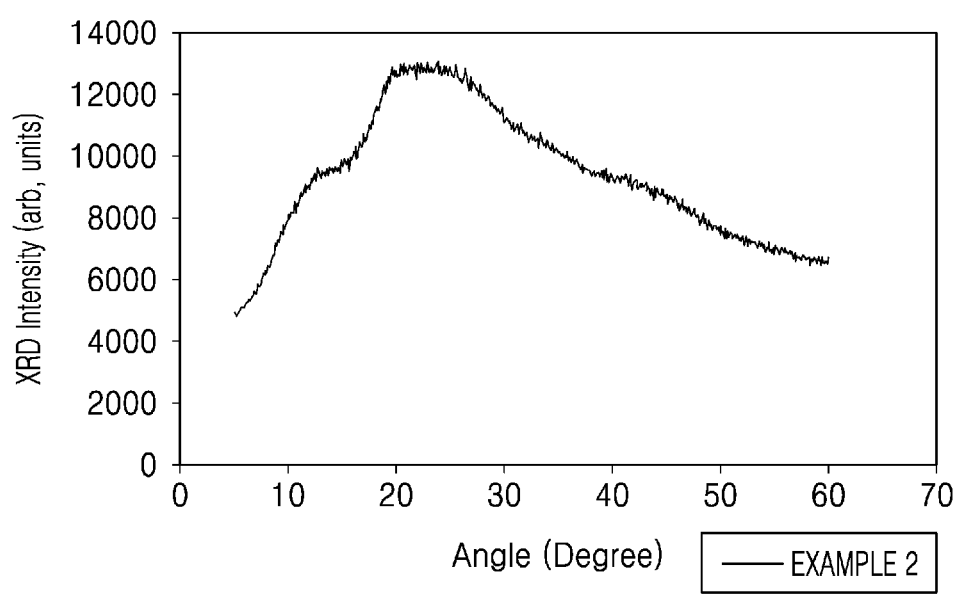
FIG. 3 shows results of X-ray powder diffraction analysis of a crosslinked hyaluronic acid product in the form of powder according to Example 2, wherein the vertical axis represents intensity (cps), and the horizontal axis represents 2θ(°)

The results of X-ray diffraction analysis are shown in FIGS. 3 to 5.

As confirmed in FIGS. 3 to 5, the crosslinked hyaluronic acid product in the form of powder according to Example 2 and the crosslinked hyaluronic acid hydrogels according to Examples 6 and 10 were all amorphous.

The crosslinked hyaluronic acid product in the form of powder according to Example 2 showed a gentle peak at the 2θ value of about 22° to about 23°, and each of the crosslinked hyaluronic acid hydrogels according to Examples 6 and 10 showed a gentle peak at the 2θ value of about 28°.

Example 12

An equivalent amount of ethanol was added to a 1% aqueous NaOH solution, and sodium hyaluronate (Na-HA, molecular weight: 1.0 MDa to 4.0 MDa) was added thereto such that a concentration of the mixture was 3% (w/v). BDDE was added thereto to prepare a reaction product. In this regard, a ratio of BDDE and sodium hyaluronate (Na-HA) was 100 μL (BDDE)/1 g (HA).

This reaction product was subjected to a crosslinking reaction by stirring at 30° C. and 200 rpm or less for 5 hours. Ethanol was added thereto at a rate of 100 mL/min or less until a volume ratio of the reaction product and ethanol was 1:5. Sodium hyaluronate (Na-HA) was precipitated in the form of powder, and then the precipitate was further subjected to a crosslinking reaction for 16 hours. After the crosslinking reaction, a 1.2 M HCl solution was added to adjust pH (pH 8 or less) to terminate the reaction, followed by washing with ethanol several times.

After washing, the product was dried at a loss of dry weight of 10% or less to obtain a crosslinked hyaluronic acid product in the form of powder. The crosslinked hyaluronic acid product was added to PBS at 10 mg/mL to obtain a hydrogel. The hydrogel was homogenized using a homogenizer at 7000 rpm or less. The homogenized gel was sterilized at 121° C. for 20 minutes or shorter to obtain a crosslinked hyaluronic acid hydrogel.

Example 13

A crosslinked hyaluronic acid product in the form of powder was prepared in the same manner as in Example 12, except that sodium hyaluronate (Na-HA) was added to the mixed solution of 1% aqueous NaOH solution and ethanol such that a concentration of the mixture was 2% (w/v), and BDDE was added thereto at a ratio of BDDE to sodium hyaluronate (Na-HA) of 125 µl (BDDE)/1 g (HA) to prepare a reaction product.

Experimental Example 6: Evaluation of Storage Stability of Crosslinked Hyaluronic Acid Hydrogel and Measurement of Viscoelasticity (3)

The crosslinked hyaluronic acid hydrogels prepared in Examples 12 and 13 were stored at 25° C., 30° C., 40° C., and 60° C. for 8 months, respectively while viscoelasticity thereof was periodically measured every one month. The measurement of viscoelasticity was performed using a KINEXUS™ Pro Rheometer (Malvern, Worchestershire, UK) which is a rotational rheometer under the same conditions as in Experimental Example 1. Further, a commercially available crosslinked hyaluronic acid product injection SYNVISC-ONE® (Sanofi) was used as a comparative product and viscoelasticity thereof was measured under the same conditions. In Table 5 and Table 6, values not measured (blank=Not measured) after the experiment was completed are marked with *.

The results of measuring elasticity and viscosity of the hydrogels according to Examples 12 and 13 and the comparative product are shown in Tables 5 to 7, and FIGS. 6 to 11.

TABLE 5

Results of elasticity according to temperature and storage period

| STORAGE PERIOD | 0M | 1M | 2M | 3M | 4M | 5M | 6M | 7M | 8M |
|---|---|---|---|---|---|---|---|---|---|
| EXAMPLE 12 | | | | | | | | | |
| 25° C. | 118.0 | 133.0 | 136.7 | 117.1 | 112.1 | 110.6 | 96.8 | 92.4 | 107.9 |
| 30° C. | 118.0 | 143.0 | 134.6 | 122.6 | 121.9 | 121.9 | 128.0 | 113.9 | 118.7 |
| 40° C. | 118.0 | 147.7 | 123.0 | 116.3 | 113.3 | 112.1 | 112.1 | 105.3 | 108.8 |
| 60° C. | 118.0 | 124.2 | 106.0 | 76.1 | 65.6 | * | * | * | * |
| EXAMPLE 13 | | | | | | | | | |
| 25° C. | 68.7 | 77.0 | 76.1 | 65.9 | 63.7 | 59.6 | 60.0 | 57.2 | 57.1 |
| 30° C. | 68.7 | 75.4 | 73.5 | 63.5 | 66.6 | 64.4 | 66.9 | 66.7 | 65.5 |
| 40° C. | 68.7 | 65.8 | 71.9 | 60.8 | 56.2 | 51.5 | 55.5 | 50.9 | 50.1 |
| 60° C. | 68.7 | 55.8 | 47.4 | 32.3 | 24.3 | * | * | * | * |
| COMPARATIVE PRODUCT (SYNVISC-ONE ®) | | | | | | | | | |
| 25° C. | 118.0 | 120.7 | 108.7 | 105.8 | 101.7 | 102.5 | 81.3 | * | * |
| 30° C. | 118.0 | 112.4 | 103.7 | 101.3 | 103.6 | 103.2 | 90.8 | * | * |
| 40° C. | 118.0 | 116.0 | 97.8 | 90.5 | 87.9 | 78.0 | 70.1 | * | * |
| 60° C. | 118.0 | 59.7 | 25.9 | 16.1 | 11.1 | * | * | * | * |

TABLE 6

Results of viscosity according to temperature and storage period

| STORAGE PERIOD | 0M | 1M | 2M | 3M | 4M | 5M | 6M | 7M | 8M |
|---|---|---|---|---|---|---|---|---|---|
| EXAMPLE 12 | | | | | | | | | |
| 25° C. | 21.3 | 24.1 | 24.7 | 21.3 | 20.7 | 20.7 | 18.1 | 17.6 | 20.2 |
| 30° C. | 21.3 | 24.7 | 23.6 | 21.8 | 21.3 | 21.5 | 22.7 | 20.9 | 20.8 |
| 40° C. | 21.3 | 25.5 | 21.8 | 21.1 | 20.8 | 20.6 | 21.3 | 20.2 | 20.3 |
| 60° C. | 21.3 | 23.4 | 22.6 | 17.2 | 16.0 | * | * | * | * |
| EXAMPLE 13 | | | | | | | | | |
| 25° C. | 24.5 | 24.3 | 27.2 | 23.9 | 23.3 | 22.2 | 22.6 | 21.5 | 21.3 |
| 30° C. | 24.5 | 26.5 | 26.1 | 22.8 | 23.2 | 19.5 | 23.9 | 23.8 | 22.8 |
| 40° C. | 24.5 | 23.9 | 26.3 | 22.6 | 21.2 | 19.7 | 21.8 | 20.2 | 20.1 |
| 60° C. | 24.5 | 21.8 | 20.5 | 15.1 | 12.8 | * | * | * | * |
| COMPARATIVE PRODUCT (SYNVISC-ONE ®) | | | | | | | | | |
| 25° C. | 23.0 | 21.1 | 18.2 | 18.8 | 18.6 | 19.0 | 14.7 | * | * |
| 30° C. | 23.0 | 20.3 | 18.6 | 18.8 | 20.1 | 19.3 | 19.0 | * | * |
| 40° C. | 23.0 | 23.3 | 21.0 | 22.2 | 23.9 | 24.3 | 23.5 | * | * |
| 60° C. | 23.0 | 25.5 | 20.1 | 14.7 | 11.5 | * | * | * | * |

TABLE 7

Modulus of viscoelasticity reduction after 8 months

| STORAGE TEMPERATURE | EXAMPLE 12 | | EXAMPLE 13 | | COMPARATIVE PRODUCT (SYNVISC-ONE ®) | |
|---|---|---|---|---|---|---|
| | MODULUS OF ELASTICITY REDUCTION | MODULUS OF VISCOSITY REDUCTION | MODULUS OF ELASTICITY REDUCTION | MODULUS OF VISCOSITY REDUCTION | MODULUS OF ELASTICITY REDUCTION | MODULUS OF VISCOSITY REDUCTION |
| 25° C. | 9.3% | 4.7% | 16.1% | 12.5% | 31.3% | 39.1% |
| 30° C. | 0.0% | 4.7% | 4.4% | 8.3% | 23.7% | 21.7% |
| 40° C. | 8.4% | 4.7% | 26.4% | 16.6% | 40.6% | 0.0% |
| 60° C. | 44.9% | 23.8% | 64.7% | 50.0% | 90.6% | 52.1% |

In Table 5, elasticity represents storage modulus (G', Pa at 2.5 Hz). In Table 6, viscosity represents loss modulus (G", Pa at 2.5 Hz). Table 7 shows a modulus of elasticity reduction and a modulus of viscosity reduction, which were measured after storing the hydrogels according to Examples 12 and 13 and the comparative product at 25° C., 30° C., 40° C., and 60° C. for 8 months, respectively.

As shown in Tables 5 and 6, and FIGS. 6 to 11, the hydrogels according to Examples 12 and 13 showed stability equivalent to or higher than that of the comparative product (Synvisc-one®). Further, in the hydrogels according to Examples 12 and 13 or the comparative product, the viscoelasticity tended to decrease, as the temperature of the storage conditions increased, and the modulus of elasticity reduction was higher than the modulus of viscosity reduction.

Example 14

Example 14-1

Ethanol was added to a 1% aqueous NaOH solution at a ratio of 6:4, and sodium hyaluronate (Na-HA, molecular weight: 1.0 MDa to 4.0 MDa) was added thereto such that a concentration of the mixture was 2.5% (w/v). BDDE was added thereto to prepare a reaction product. In this regard, a ratio of BDDE and sodium hyaluronate (Na-HA) was 100 µl (BDDE)/1 g (HA).

The reaction product was subjected to a crosslinking reaction for 5 hours by stirring at 30° C. and at a speed of 170 rpm. Ethanol was added thereto at a rate of 100 mL/min or less, until a volume ratio of the reaction product and ethanol was 1:5. Sodium hyaluronate (Na-HA) was precipitated in the form of powder, and then the precipitate was further subjected to a crosslinking reaction for 16 hours. After the crosslinking reaction, a 1.2 M HCl solution was added to adjust pH (pH 8 or less) to terminate the reaction, followed by washing with ethanol several times.

After washing, the product was dried at a loss of dry weight of 10% or less to obtain a crosslinked hyaluronic acid product in the form of powder. The crosslinked hyaluronic acid product was added to PBS at 10 mg/mL to obtain a hydrogel. The hydrogel was homogenized using a homogenizer at 7000 rpm or less. The homogenized gel was sterilized at 121° C. for 21 minutes or shorter to obtain a crosslinked hyaluronic acid hydrogel.

Example 14-2

A crosslinked hyaluronic acid product in the form of powder was prepared in the same manner as in Example 14-1, except that BDDE was added at a ratio of BDDE to sodium hyaluronate (Na-HA) of 120 µl (BDDE)/1 g (HA) to prepare a reaction product.

Example 14-2

A crosslinked hyaluronic acid product in the form of powder was prepared in the same manner as in Example 14-1, except that BDDE was added at a ratio of BDDE to sodium hyaluronate (Na-HA) of 140 µl (BDDE)/1 g (HA) to prepare a reaction product.

Example 15

Example 15-1

Ethanol was added to a 1% aqueous NaOH solution at a ratio of 6:4, and sodium hyaluronate (Na-HA, molecular weight: 1.0 MDa to 4.0 MDa) was added thereto such that a concentration of the mixture was 2.5% (w/v). BDDE was added thereto to prepare a reaction product. In this regard, a ratio of BDDE and sodium hyaluronate (Na-HA) was 120 µl (BDDE)/1 g (HA).

The reaction product was subjected to a crosslinking reaction for 5 hours by stirring at 25° C. and at a speed of 170 rpm. Ethanol was added thereto at a rate of 100 mL/min or less, until a volume ratio of the reaction product and ethanol was 1:5. Sodium hyaluronate (Na-HA) was precipitated in the form of powder, and then the precipitate was further subjected to a crosslinking reaction for 16 hours. After the crosslinking reaction, a 1.2 M HCl solution was added to adjust pH (pH 8 or less) to terminate the reaction, followed by washing with ethanol several times.

After washing, the product was dried at a loss of dry weight of 10% or less to obtain a crosslinked hyaluronic acid product in the form of powder. The crosslinked hyaluronic acid product was added to PBS at 10 mg/mL to obtain a hydrogel. The hydrogel was homogenized using a homogenizer at 7000 rpm or less. The homogenized gel was sterilized at 121° C. for 21 minutes or shorter to obtain a crosslinked hyaluronic acid hydrogel.

Example 15-2

A crosslinked hyaluronic acid product in the form of powder was prepared in the same manner as in Example 15-1, except that the reaction product was subjected to the crosslinking reaction at a reaction temperature of 30° C.

Example 15-3

A crosslinked hyaluronic acid product in the form of powder was prepared in the same manner as in Example 15-1, except that the reaction product was subjected to the crosslinking reaction at a reaction temperature of 35° C.

Example 16

Example 16-1

Ethanol was added to a 1% aqueous NaOH solution at a ratio of 6:4, and sodium hyaluronate (Na-HA, molecular weight: 1.0 MDa to 4.0 MDa) was added thereto such that a concentration of the mixture was 2.5% (w/v). BDDE was added thereto to prepare a reaction product. In this regard, a ratio of BDDE and sodium hyaluronate (Na-HA) was 120 μl (BDDE)/1 g (HA).

The reaction product was subjected to a crosslinking reaction for 5 hours by stirring at 30° C. and at a speed of 50 rpm. Ethanol was added thereto at a rate of 100 mL/min or less, until a volume ratio of the reaction product and ethanol was 1:5. Sodium hyaluronate (Na-HA) was precipitated in the form of powder, and then the precipitate was further subjected to a crosslinking reaction for 16 hours. After the crosslinking reaction, a 1.2 M HCl solution was added to adjust pH (pH 8 or less) to terminate the reaction, followed by washing with ethanol several times.

After washing, the product was dried at a loss of dry weight of 10% or less to obtain a crosslinked hyaluronic acid product in the form of powder. The crosslinked hyaluronic acid product was added to PBS at 10 mg/mL to obtain a hydrogel. The hydrogel was homogenized using a homogenizer at 7000 rpm or less. The homogenized gel was sterilized at 121° C. for 21 minutes or shorter to obtain a crosslinked hyaluronic acid hydrogel.

Example 16-2

A crosslinked hyaluronic acid product in the form of powder was prepared in the same manner as in Example 16-1, except that the stirring speed of the reaction product was 130 rpm.

Example 16-3

A crosslinked hyaluronic acid product in the form of powder was prepared in the same manner as in Example 16-1, except that the stirring speed of the reaction product was 200 rpm.

Experimental Example 7: Analysis of Degree of Crosslinking of Crosslinked Hyaluronic Acid Product Hyaluronic acid (HA) is a polysaccharide, in which glucuronic acid and N-acetyl-D-glucosamine are repeatedly connected. It is known that when hyaluronic acid is treated with *Streptomyces* hyaluronidase, it is degraded into an oligosaccharide having a 4,5-unsaturated glucuronosyl residue at a non-reducing end. Unmodified HA by complete digestion produces two products of a tetrasaccharide (tetramer) and a hexasaccharide (hexamer). Octasaccharide (octamer) is the smallest substrate for enzymatic digestion. As enzymatic digestion proceeds, HA is degraded into small units of oligosaccharides. HA modified by a crosslinking agent, such as BDDE, is in the form of oligosaccharides (HA-BDDE-HA, HA-BDDE), in which the crosslinking agent is bound, even when degraded by enzyme. Thus, there is a difference in the retention time between the unmodified HA and the modified HA during HPLC analysis.

Therefore, the degree of modification by binding of the crosslinking agent to hyaluronic acid was regarded as degree of modification (MoD), crosslinking of hyaluronic acid (HA-BDDE-HA) on both sides of the crosslinking agent was regarded as crosslink MoD, and crosslinking of hyaluronic acid on one side of the crosslinking agent (HA-BDDE) was regarded as pendant MoD.

The hyaluronidase (derived from *Streptomyces* hyaluroiyticus) used in the digestion of hyaluronic acid (HA) was a product of Merck (Sigma Aldrich). A column for HPLC analysis was DIONEX CARBOPAC™ PA100 (Thermo Scientific).

HA modified by the crosslinking agent was digested using hyaluronidase under conditions of pH 5.0 and 36° C. The digested HA was distinctly separated into a tetramer, a hexamer, and higher-order oligomers using an HPLC system. The size of each separated peak was compared by UV absorbance at 232 nm. When hyaluronic acid is completely digested with hyaluronidase, it produces a tetramer and a hexamer, and crosslinked hyaluronic acid produces saccharide units slightly larger than the tetramer and hexamer, or oligomers larger than those, etc., which are shown in chromatograms. MoD may be obtained by the area of each chromatogram, and peaks of higher-order oligomers larger than octamers may be distinguished by crosslink MoD (%), and peaks of oligomers smaller than octamers, excluding main peaks of tetramer and hexamer, may be distinguished by pendant MoD (%), and both of them are combined as total MoD (%).

The degree of crosslinking of the crosslinked hyaluronic acid product prepared in Example 12, SYNVISC-ONE® (Sanofi) used as a comparative product, and natural hyaluronic acid (HA) was analyzed and shown in Table 8. The degree of crosslinking of the crosslinked hyaluronic acid products prepared in Examples 14-1 to 16-3 was analyzed and shown in Table 9.

TABLE 8

| SECTION | | EXAMPLE 12 | COMPARATIVE PRODUCT (SYNVISC-ONE ®) | NATURAL HA (UNMODIFIED) |
|---|---|---|---|---|
| PHYSICAL PROPERTIES | G'(Pa) | 118 | 118 | — |
| | G" (Pa) | 27 | 23 | — |
| | HA CONCENTRATION (mg/mL) | 10 | 8 | — |
| PREPARATION CONDITIONS | IPC (%) | 3.0 | No data | — |
| | BDDE / HA (μL/g) | 100 | No data | — |
| | TEMPERATURE (° C.) | 30 | No data | — |
| | NaOH RATIO (%) | 0.5 | No data | — |
| | EtOH RATIO (%) | 50 | No data | — |

TABLE 8-continued

| SECTION | | EXAMPLE 12 | COMPARATIVE PRODUCT (SYNVISC-ONE ®) | NATURAL HA (UNMODIFIED) |
|---|---|---|---|---|
| ANALYSIS OF DEGREE OF MODIFICATION | TETRAMER (%) | 57.1 | 57.4 | 57.8 |
| | HEXAMER (%) | 40.7 | 40.3 | 41.6 |
| | PENDANT MoD (%) | 0.90 | 1.25 | 0.46 |
| | CROSSLINK MoD (%) | 1.31 | 1.07 | 0.19 |
| | TOTAL MoD (%) | 2.21 | 2.32 | 0.65 |

TABLE 9

| SECTION | | EXAMPLE 14-1 | EXAMPLE 14-2 | EXAMPLE 14-3 | EXAMPLE 15-1 | EXAMPLE 15-2 | EXAMPLE 15-3 | EXAMPLE 16-1 | EXAMPLE 16-2 | EXAMPLE 16-3 |
|---|---|---|---|---|---|---|---|---|---|---|
| PHYSICAL PROPERTIES | G' (Pa) | 138.9 | 151.4 | 154.0 | 139.2 | 117.5 | — | 84.6 | 134.8 | 81.7 |
| | G" (Pa) | 18.2 | 18.3 | 21.6 | 19.3 | 20.3 | — | 12.4 | 23.4 | 14.6 |
| | HA CONCENTRATION (mg/mL) | 10 | 10 | 10 | 10 | 10 | 10 | 10 | 10 | 10 |
| CONTROL PARAMETER | IPC (%) | 2.5 | 2.5 | 2.5 | 2.5 | 2.5 | 2.5 | 2.5 | 2.5 | 2.5 |
| | BDDE/HA (μL/g) | 100 | 120 | 140 | 120 | 120 | 120 | 120 | 120 | 120 |
| | STIRRING SPEED (rpm) | 170 | 170 | 170 | 170 | 170 | 170 | 50 | 130 | 200 |
| | TEMPERATURE (° C.) | 30 | 30 | 30 | 25 | 30 | 35 | 30 | 30 | 30 |
| | NaOH RATIO (%) | 0.6 | 0.6 | 0.6 | 0.6 | 0.6 | 0.6 | 0.6 | 0.6 | 0.6 |
| | EtOH RATIO (%) | 40 | 40 | 40 | 40 | 40 | 40 | 40 | 40 | 40 |
| ANALYSIS OF DEGREE OF MODIFICATION (MoD) | TETRAMER (%) | 57.2 | 57.2 | 57.0 | 57.2 | 57.2 | 56.9 | 56.9 | 57.0 | 57.0 |
| | HEXAMER (%) | 40.6 | 40.4 | 40.3 | 40.9 | 40.7 | 40.3 | 40.5 | 40.5 | 40.5 |
| | PENDANT MoD (%) | 0.86 | 0.92 | 0.96 | 0.71 | 0.78 | 0.84 | 0.92 | 0.92 | 0.88 |
| | CROSSLINK MoD (%) | 1.40 | 1.49 | 1.75 | 1.22 | 1.36 | 1.93 | 1.65 | 1.57 | 1.59 |
| | TOTAL MoD (%) | 2.25 | 2.42 | 2.71 | 1.92 | 2.14 | 2.77 | 2.57 | 2.49 | 2.47 |

As shown in Table 8, the crosslinked hyaluronic acid product prepared in Example 12 showed viscoelasticity similar to and stability equivalent to or higher than those of the comparative product Synvisc-one®. Further, the crosslinked hyaluronic acid product prepared in Example 12 showed increased pendant MoD (%), crosslink MoD (%), and total MoD (%), as compared with natural hyaluronic acid(HA). Further, the crosslinked hyaluronic acid product prepared in Example 12 showed pendant MoD (%), crosslink MoD (%), and total MoD (%) equivalent to or higher than those of Synvisc-one®.

As shown in Table 9, MoD (%) increased, as more crosslinking reactions occurred. In general, the crosslinking reaction increased, as the addition amount of crosslinking agent (a molar ratio of BDDE:HA) increased, and MoD (or degree of modification, degree of crosslinking) (%) increased, as the crosslinking reaction increased. For example, the results of analyzing the degree of crosslinking of the crosslinked hyaluronic acid products according to Examples 14-1 to 14-3, which were prepared by varying the concentration of the crosslinking agent (e.g., BDDE), showed that MoD (%) increased, as the concentration of the crosslinking agent increased.

Further, as shown in Table 9, the results of analyzing the degree of crosslinking of the crosslinked hyaluronic acid products according to Examples 15-1 to 15-3, which were prepared by varying the reaction temperature, showed that MoD (%) increased, as the reaction temperature increased. Meanwhile, the results of analyzing the degree of crosslinking of the crosslinked hyaluronic acid products according to Examples 16-1 to 16-3, which were prepared by varying the stirring speed (5 hours or shorter after adding BDDE) during the crosslinking reaction, showed that there was no great difference in MoD (%) according to the stirring speed.

In general, as MoD (%) value increased, viscoelasticity, i.e., elasticity represented by storage modulus (G', Pa at 2.5 Hz) and viscosity represented by loss modulus (G", Pa at 2.5 Hz) increased. However, the viscoelasticity value did not always show a constant trend, because it is affected by other factors such as formulation, etc.

Hereinabove, the present disclosure has been described with reference to exemplary embodiments thereof. It will be understood by those skilled in the art to which the present disclosure pertains that the present disclosure may be implemented in modified forms without departing from the spirit and scope of the present disclosure. Therefore, exemplary embodiments disclosed herein should be considered in an illustrative aspect rather than a restrictive aspect. The scope of the present disclosure should be defined by the claims rather than the above-mentioned description, and equivalents to the claims should be interpreted to fall within the present disclosure.

The invention claimed is:

1. A method of preparing a crosslinked hyaluronic acid product in a form of powder, the method comprising:
    preparing an aqueous solution comprising hyaluronic acid, a salt thereof, or a mixture thereof;
    adding a crosslinking agent to the aqueous solution to cause a first crosslinking reaction of the hyaluronic acid to occur for 4 to 6 hours;
    adding ethanol to the aqueous solution to solidify the hyaluronic acid to produce a mixed solution comprising hyaluronic acid particles, wherein, when the ethanol is added, a rate of volume change of the ethanol with respect to a total volume of the mixed solution is 0.5% (v/v)/min to 35% (v/v)/min; and
    performing a second crosslinking reaction by crosslinking the mixed solution comprising hyaluronic acid particles to prepare a crosslinked hyaluronic acid product for 6 to 24 hours,
    washing and drying the crosslinked hyaluronic acid product to obtain the crosslinked hyaluronic acid product in a form of a powder,
    wherein the crosslinked hyaluronic acid product exhibits a particle size distribution D90 of 80 μm or less.

2. The method of claim 1, wherein, when ethanol is added to the aqueous solution, the ethanol is added at a rate of 20 mL/min to 1000 mL/min.

3. The method of claim 1, wherein the crosslinking agent is in an amount of 10 μL to 500 μL with respect to 1 g of hyaluronic acid, a salt thereof, or a mixture thereof.

4. The method of claim 1, wherein a volume ratio of the aqueous solution and ethanol added to the aqueous solution is 1:1 to 1:10.

5. The method of claim 1, wherein washing is performed with ethanol or a solution comprising ethanol.

6. A method of preparing a crosslinked hyaluronic acid hydrogel, the method comprising:
    preparing an aqueous solution comprising hyaluronic acid, a salt thereof, or a mixture thereof;
    adding a crosslinking agent to the aqueous solution to cause a first crosslinking reaction of the hyaluronic acid to occur for 4 to 6 hours;
    adding ethanol to the aqueous solution to solidify the hyaluronic acid to produce a mixed solution comprising hyaluronic acid particles, wherein, when the ethanol is added, a rate of volume change of the ethanol with respect to a total volume of the mixed solution is 0.5% (v/v)/min to 35% (v/v)/min;
    performing a second crosslinking reaction of the mixed solution comprising the hyaluronic acid particles to prepare a crosslinked hyaluronic acid product for 6 to 24 hours; and
    hydrating the crosslinked hyaluronic acid product to prepare a crosslinked hyaluronic acid hydrogel,
    wherein the crosslinked hyaluronic acid hydrogel exhibits a particle size distribution D90 of 240 μm or less, and
    wherein the crosslinked hyaluronic acid hydrogel exhibits elasticity of 30 Pa to 200 Pa and viscosity of 10 Pa to 100 Pa.

7. The method of claim 6, wherein the hydration is performed by adding the crosslinked hyaluronic acid product to water or a solution comprising water.

8. The method of claim 6, wherein 5 mg to 15 mg of the crosslinked hyaluronic acid product is added to 1 mL of water or a solution comprising water.

9. The method of claim 6, further comprising filtering the crosslinked hyaluronic acid hydrogel using a filter.

10. A crosslinked hyaluronic acid hydrogel, prepared by a method comprising:
    preparing an aqueous solution comprising hyaluronic acid, a salt thereof, or a mixture thereof;
    adding a crosslinking agent to the aqueous solution to cause a first crosslinking reaction of the hyaluronic acid to occur for 4 to 6 hours;
    adding ethanol to the aqueous solution to solidify the hyaluronic acid to produce a mixed solution comprising hyaluronic acid particles, wherein, when the ethanol is added, a rate of volume change of the ethanol with respect to a total volume of the mixed solution is 0.5% (v/v)/min to 35% (v/v)/min;
    performing a second crosslinking reaction of the mixed solution comprising the hyaluronic acid particles to prepare a crosslinked hyaluronic acid product for 6 to 24 hours;
    hydrating the crosslinked hyaluronic acid product to obtain a crosslinked hyaluronic acid hydrogel; and
    filtering the crosslinked hyaluronic acid hydrogel,
    wherein the crosslinked hyaluronic acid hydrogel obtained after filtering exhibits a particle size distribution D90 of 120 μm or less, and
    wherein the crosslinked hyaluronic acid hydrogel obtained after filtering exhibits elasticity of 30 Pa to 200 Pa and viscosity of 10 Pa to 100 Pa.

11. The crosslinked hyaluronic acid hydrogel of claim 10, wherein the crosslinked hyaluronic acid hydrogel obtained after filtering exhibits particle size distributions D10 of 10 μm to 30 μm, D50 of 35 μm to 65 μm, and D90 of 80 μm to 120 μm.

12. The crosslinked hyaluronic acid hydrogel of claim 10, wherein the crosslinking agent is butanediol diglycidyl ether (BDDE), divinyl sulfone (DVS), or a mixture thereof.

13. The method of claim 1, wherein the crosslinked hyaluronic acid product exhibits particle size distributions D10 of 2.5 μm to 6 μm, D50 of 8 μm to 20 μm, and D90 of 25 μm to 80 μm.

14. The method of claim 6, wherein the crosslinked hyaluronic acid hydrogel exhibits particle size distributions D10 of 25 μm to 40 μm, D50 of 70 μm to 110 μm, and D90 of 190 μm to 240 μm.

* * * * *